US011806025B2

(12) United States Patent
Solitro et al.

(10) Patent No.: US 11,806,025 B2
(45) Date of Patent: Nov. 7, 2023

(54) METHOD, DEVICE, AND SYSTEM FOR BONE FIXATION

(71) Applicant: Board of Supervisors of Louisiana State University and Agricultural and Mechanical College, Baton Rouge, LA (US)

(72) Inventors: Giovanni Francesco Solitro, Shreveport, LA (US); R. Shane Barton, Shreveport, LA (US); Johnathan Steven Alexander, Shreveport, LA (US)

(*) Notice: Subject to any disclaimer, the term of this patent is extended or adjusted under 35 U.S.C. 154(b) by 0 days.

(21) Appl. No.: 17/111,048

(22) Filed: Dec. 3, 2020

(65) Prior Publication Data

US 2022/0071642 A1    Mar. 10, 2022

Related U.S. Application Data

(60) Provisional application No. 62/942,202, filed on Dec. 1, 2019.

(51) Int. Cl.
*A61B 17/16* (2006.01)
*A61B 17/17* (2006.01)

(52) U.S. Cl.
CPC ...... *A61B 17/1637* (2013.01); *A61B 17/1615* (2013.01); *A61B 17/1728* (2013.01); *A61B 17/1739* (2013.01)

(58) Field of Classification Search
CPC ..... A61B 17/17; A61B 17/15; A61B 17/1615; A61B 17/1728; A61B 17/1739; A61B 17/1637
See application file for complete search history.

(56) References Cited

U.S. PATENT DOCUMENTS

| 2003/0009170 | A1* | 1/2003 | Tornier | A61B 17/1739 606/87 |
| 2008/0208249 | A1* | 8/2008 | Blain | A61B 17/1608 606/205 |
| 2011/0184426 | A1* | 7/2011 | Garces | A61B 17/808 606/104 |
| 2016/0113720 | A1* | 4/2016 | Lavallee | A61B 17/15 901/9 |

* cited by examiner

*Primary Examiner* — Kevin T Truong
*Assistant Examiner* — Diana Jones
(74) *Attorney, Agent, or Firm* — Jones Walker LLP

(57) ABSTRACT

The presently disclosed invention relates to devices and methods for conducting bone surgery on an animal using a bone surgery tool comprising a base, a fixed arm fixed to the base, the fixed arm including a shoulder and a jaw, a sliding arm releasably fixable to the base, the sliding arm including a head that receives an implant and a cartridge in a slot, the method comprising hooking the bone with the jaw, moving the head toward the jaw capturing the bone, accessing the bone with a drill through cartridge bores in the cartridge, and drilling holes, accessing the bone with a self-shearing screw attached to a screw driver through cartridge bores in the cartridge, and attaching the implant to the bone, and moving the head away from the jaw releasing the bone.

16 Claims, 30 Drawing Sheets

METHOD, DEVICE, AND SYSTEM FOR BONE FIXATION

CROSS REFERENCE TO RELATED APPLICATIONS/PRIORITY

The present invention claims priority to U.S. Provisional Patent Application No. 62/942,202 filed Dec. 1, 2019, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Animal fracture models have been widely adopted for the purpose of refining and expanding bone healing and recovery. In an attempt to improve reproducibility, fixation implants have been miniaturized for murine (mouse) models with tools for their implantation. Despite the level of detail of the manufactured implants, a current implantation method remains complex and technically challenging, requiring the execution of several tasks by at least two simultaneous operators. One current method includes drilling a single hole first before separately using a guide for other holes. The method includes requiring two users are to cut the bone and obtain a final construct.

SUMMARY

Wherefore, it is an object of the present invention to overcome the above-mentioned shortcomings and drawbacks associated with the current technology. The present invention is directed to methods and apparatuses that satisfy the above shortcomings and drawbacks.

The presently disclosed invention relates to methods and bone surgery tools comprising a base, a fixed arm fixed to the base; a sliding arm releasably fixable to the base, wherein the fixed arm includes a shoulder and a jaw and the sliding arm includes a head. According to a further embodiment, the bone surgery tool of claim includes a cartridge sized to be received by a slot defined by an inner wall of the head. According to a further embodiment, the bone surgery tool of claim includes one or more snap retainers adjacent a front entrance of the slot sized to releasably retain an implant. According to a further embodiment, the cartridge has a plurality of bore holes defined within that align to a respective plurality of screw holes in an implant when the implant and cartridge and implant are both loaded into the slot. According to a further embodiment, the bone surgery tool of claim includes a cartridge lock that releasably holds the cartridge in a fixed position relative to the head. According to a further embodiment, the bone surgery tool of claim includes a sliding arm lock that releasably holds the sliding arm in a fixed position relative to the fixed arm. According to a further embodiment, the bone surgery tool of claim includes a first and second block defining a pair of tracks positioned on a bottom surface of the housing and defining a channel in each block, and a first and second track positioned on respective sides of the shoulder such that each track makes with a channel when the sliding arm moves toward the fixed arm. According to a further embodiment, the bone surgery tool of claim includes a first and a second buffer positioned on respective first and second lateral exterior surfaces of the head. According to a further embodiment, the bone surgery tool of claim includes a bumper portion of each buffer extending forward from the head toward the jaw. According to a further embodiment, each bumper has a cutout portion. According to a further embodiment, each bumper is shaped with two substantially semi-circular cross sections, with a convex portion of each facing away from a rear opening of the slot. According to a further embodiment, the bone surgery tool of claim includes a tunnel groove for sawing a bone, the tunnel groove running from a rear facing surface of the shoulder as a tunnel, and transitions to a groove on a radially inner facing surface of the jaw, and exits at a groove exit defined in the jaw. According to a further embodiment, the shoulder has a substantially planar top surface that merges into the jaw. According to a further embodiment, the jaw curves around in a substantially circular shape defining an arc of between one half and one sixth of a circumference of a circle. According to a further embodiment, the bone surgery tool of claim includes a removeable handle. According to a further embodiment, the bone surgery tool of claim includes a helve adjacent a rear portion of the sliding arm. According to a further embodiment, the helve includes a push surface facing substantially away from the head and a ridge. According to a further embodiment, the cartridge has a cartridge insert that is sized to fit into the slot, a cartridge collar at a rear portion of the cartridge that flares outward substantially orthogonally from the cartridge insert, wider than the slot, and a hilt that extends off on one side of the cartridge.

The presently disclosed invention further relates to devices and methods for conducting bone surgery on an animal using a bone surgery tool comprising a base, a fixed arm fixed to the base, the fixed arm including a shoulder and a jaw, a sliding arm releasably fixable to the base, the sliding arm including a head that receives an implant and a cartridge in a slot, the method comprising hooking the bone with the jaw, moving the head toward the jaw capturing the bone, accessing the bone with a drill through cartridge bores in the cartridge, and drilling holes, accessing the bone with a self-shearing screw attached to a screw driver through cartridge bores in the cartridge, and attaching the implant to the bone, and moving the head away from the jaw releasing the bone.

The presently disclosed invention further relates to methods bone surgery tools comprising a base, a fixed arm fixed to the base, a sliding arm releasably fixable to the base, wherein the fixed arm includes a shoulder and a jaw, the base includes a head, and the shoulder has a substantially planar top surface that merges into the jaw, and the jaw curves around in a substantially circular shape defining an arc of between one half and one sixth of a circumference of a circle, a cartridge sized to be received by a slot defined by an inner wall of the head, one or more snap retainers adjacent a front entrance of the slot sized to releasably retain an implant, wherein the cartridge has a plurality of bore holes defined within that align to a respective plurality of screw holes in an implant when the implant and cartridge and implant are both loaded into the slot, a cartridge lock that releasably holds the cartridge in a fixed position relative to the head, a sliding arm lock that releasably holds the sliding arm in a fixed position relative to the fixed arm, a first and second block defining a pair of tracks positioned on a bottom surface of the housing and defining a channel in each block, and a first and second track positioned on respective sides of the shoulder such that each track makes with a channel when the sliding arm moves toward the fixed arm, a first and a second buffer positioned on respective first and second lateral exterior surfaces of the head, a bumper portion of each buffer extending forward from the head toward the jaw, wherein each bumper has a cutout portion, and each bumper is shaped with two substantially semicircular cross sections, with a convex portion of each facing away from a rear opening of the slot, a tunnel groove for sawing a bone, the tunnel groove running from a rear facing surface of the shoulder as a tunnel, and transitions to a groove on a radially inner facing surface of the jaw, and exits at a groove exit defined in the jaw, a handle removable from the base, a helve adjacent a rear portion of the sliding arm, the helve including a push surface facing substantially away from the head and a ridge, the cartridge has a cartridge insert that is sized to fit into the slot, a cartridge collar at a rear portion of the cartridge that flares outward substantially orthogonally from the cartridge insert, wider than the slot, and a hilt that extends off on one side of the cartridge; a brace mount connected to the base; and an adjustable bracing that connects the brace mount to a surgical surface.

The presently disclosed invention further relates to guidance in microsurgery, fracture modeling and fixation in animal models, surgical bone fixation, trauma, bone drilling, and mouse fixation.

Unlike the prior technology, some embodiments of the disclosed bone surgery tool invention have multiple advantages, including providing drilling trajectories for all the screws in the bone fixator implant as the guiding cartridge is temporarily fixed onto the bone and holds its fixed relative position during surgeries. Embodiments of the disclosed invention also allow a large number of templates for bone drilling and fixation to be performed after drilling. The disclosed methods also avoid the need for separately drilling a first screw hole which allows less experienced users to successfully perform a fixation. The disclosed methods increase the success rate with the procedure, reduces time to accomplish the procedure and is less expensive to implement compared to current models. The disclosed methods avoid the need for first drilling pilot holes prior to the drilling of the remaining holes, the need for a second user to hold the bone in place during this procedure, and the need for a second user to obtain a final construct.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that FIGS. 1-2, and 10-30 of the accompanying drawings are to scale for various embodiments of the disclosed invention, but the emphasis is instead placed on illustrating the principles of the invention. The invention will now be described, by way of example, with reference to the accompanying drawings in which:

FIG. 20 is a partial up-close isomeric view of the bone surgery tool in

FIG. 19;

DETAILED DESCRIPTION

Figure 1:
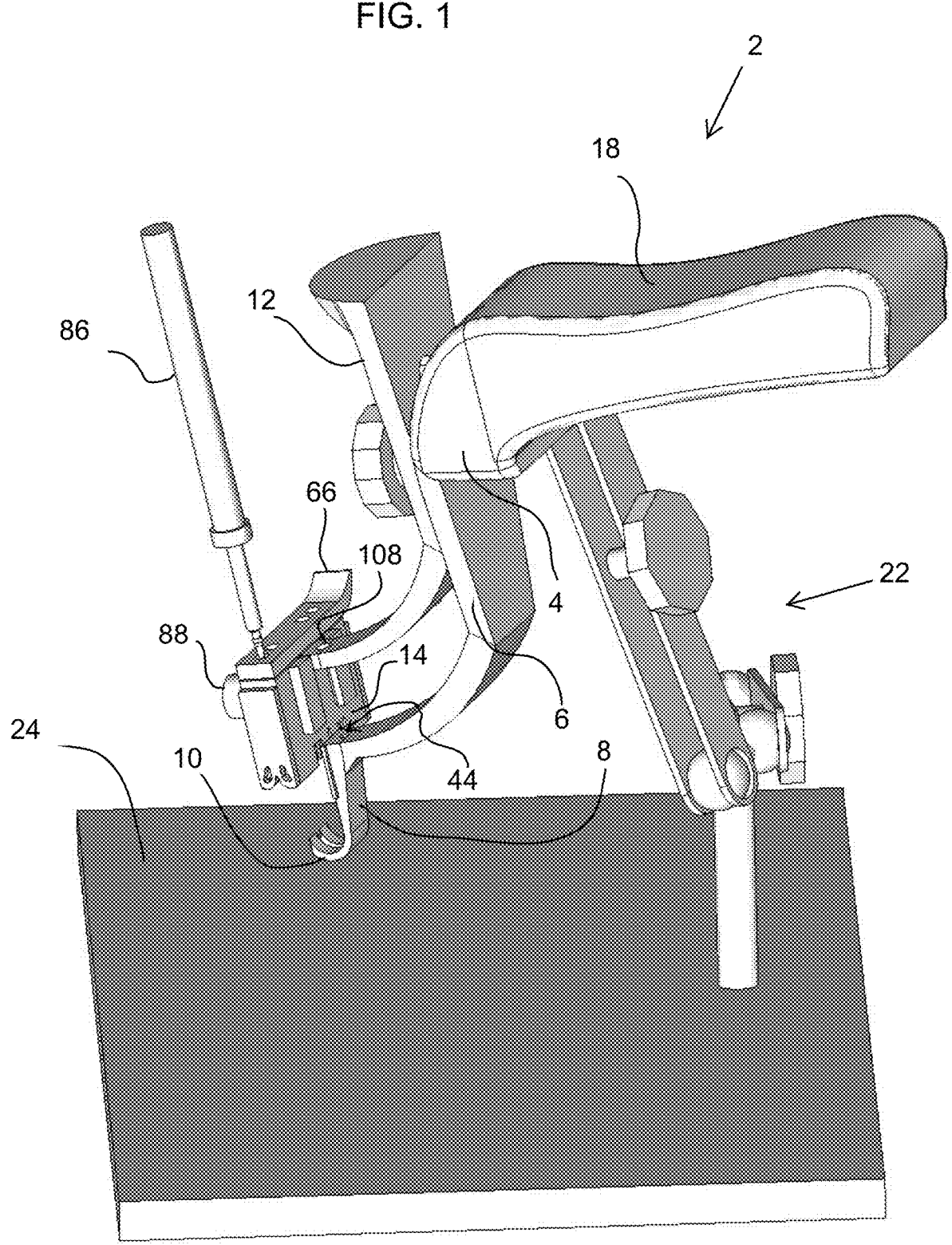
FIG. 1 is an isomeric view of an embodiment of the bone surgery tool as presently disclosed, with the bone surgery tool in a disengaged position.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-30, a brief description concerning the various components of the present invention will now be briefly discussed. As can be seen in the embodiment of FIG. 1, the bone surgery tool 2 comprises a base 4, a fixed arm 6 having a shoulder 8 and a jaw 10, and a sliding arm 12 having a head 14 and a slot 16. The base 4 and the fixed arm 6 may be of unitary construction. The fixed arm 6, including the jaw 10 and shoulder 8, may be of unitary construction. The sliding arm 12, including the head 14, may be of unitary construction.

The base 4 preferably includes a removable handle 18, sized and shaped to fit in the palm of an adult human's hand. Additionally, the base 4 preferably includes brace mount 20, such as a side ball that can snap into a ball and socket variable position or other type of adjustable bracing 22. The adjustable bracing 22 is preferably attached to a surgical surface 24. The handle 18 is preferably for positioning the bone surgery tool 2 into the correct position with regards to the animal 26 and bone 28, and then adjustable bracing 22 is locked in place, allowing hands free operation. Once the adjustable bracing 22 is locked, the handle 18 is preferably removed, providing for a more unobstructed work space for the surgeon. In the embodiment shown, the handle has a pin 29 and the base a tail 31 for a selectively removable, but friction retaining joint that securely allows pivoting of the bone surgery tool 2 in all directions when the pin 29 is mated with the tail 31.

The fixed arm 6 extends from the base 4, preferably in both a forward and vertically upward direction along a fixed neck 30 of the fixed arm 6 and at an upper portion, spaced from the base 4, the fixed arm 6 contains a shoulder 8 and jaw 10. The shoulder 8 has a top shoulder surface 32 that is substantially planar and a bottom shoulder surface 34 that angle upwards towards the top shoulder surface 32 moving in a forward direction away from the base 4. The shoulder 8 then merges into the jaw 10, and the jaw 10 curves around in preferably a substantially circular shape, preferably defining an arc of between one third and one fifth of a circumference of a circle, more preferably defining an arc of one fourth of a circumference of a circle. Rearward on both lateral sides of the shoulder is a track 36. The tracks 36 have top surfaces that are preferably parallel planar with the top shoulder surface 32, and more preferably coplanar with the top shoulder surface 32. The tracks 36 aid in maintaining stability and structural integrity of the bone surgery tool 2 when in use, by mating with respective channels 38 on blocks 40 attached to a bottom surface of the head 14. Unless otherwise noted, directions in the disclosure are in relation to the key on FIG. 25.

In a rear surface of the shoulder 8, a tunnel entrance 42 to a tunnel groove 44 is preferably provided. The tunnel groove 44 extends substantially linearly through the shoulder 8 from the tunnel entrance 42 to the transition to the jaw 10 portion of the tunnel grove 42. The tunnel groove path 46 through the jaw 10 is defined as a groove on a radially inner surface 48 of the jaw, and a groove exit 50 preferably being defined by a first chamfered semicircle edge 51 defined in the center top rear edge of the jaw 10 and a second chamfered semicircle edge 53 defined in the center top front edge of the head 14. A bottom front edge of the head 14 is also preferably a third chamfered edge 55 to allow space for the tunnel groove 44 as it exits the shoulder 8. The tunnel groove 44 may be used to precisely cut a clasped bone 28, as will be described further below.

Figure 2:
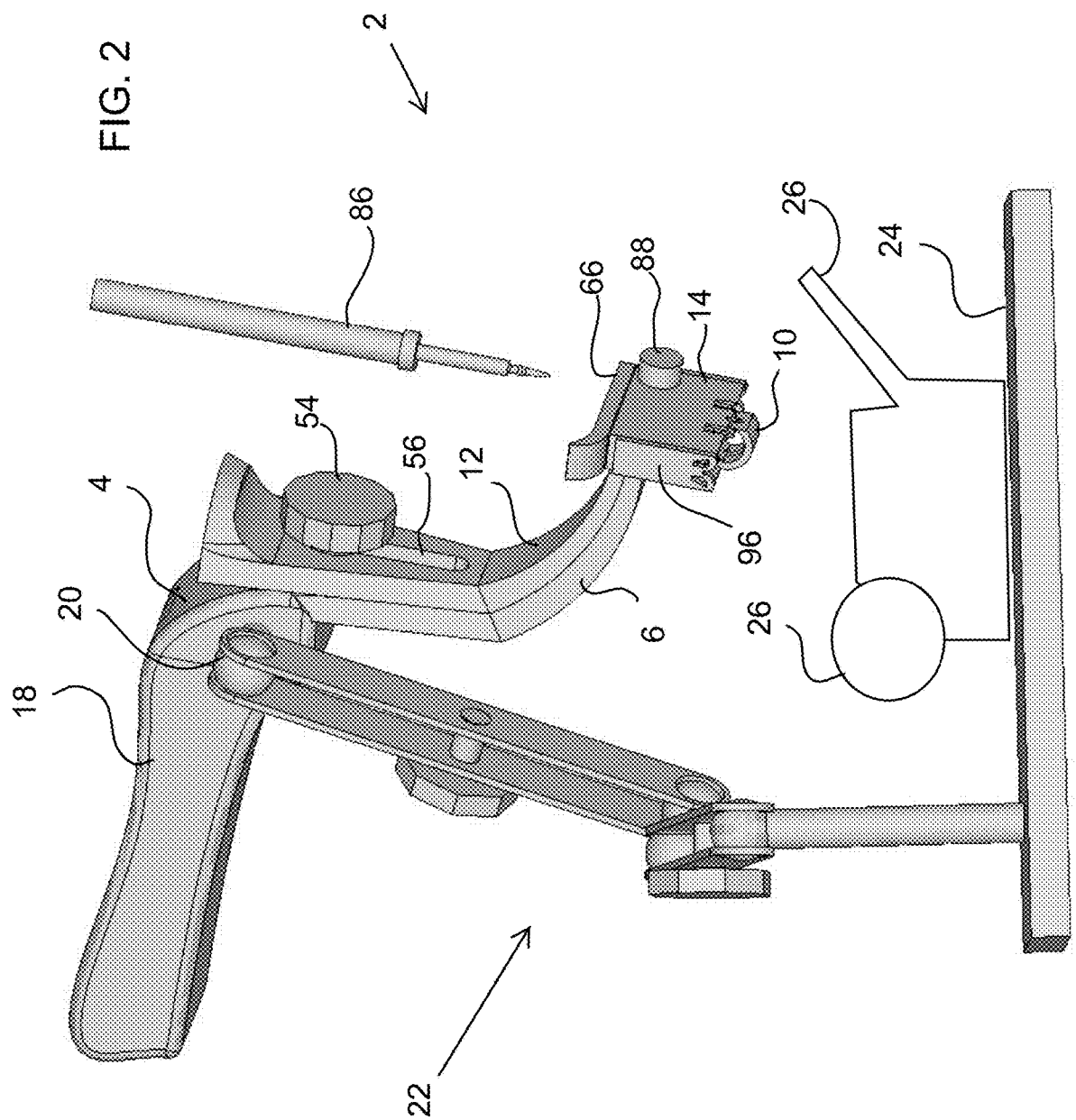
FIG. 2 is an isomeric view of the bone surgery tool in FIG. 1, though in an engaged position, with a diagram representation of an animal.
Figure 3:
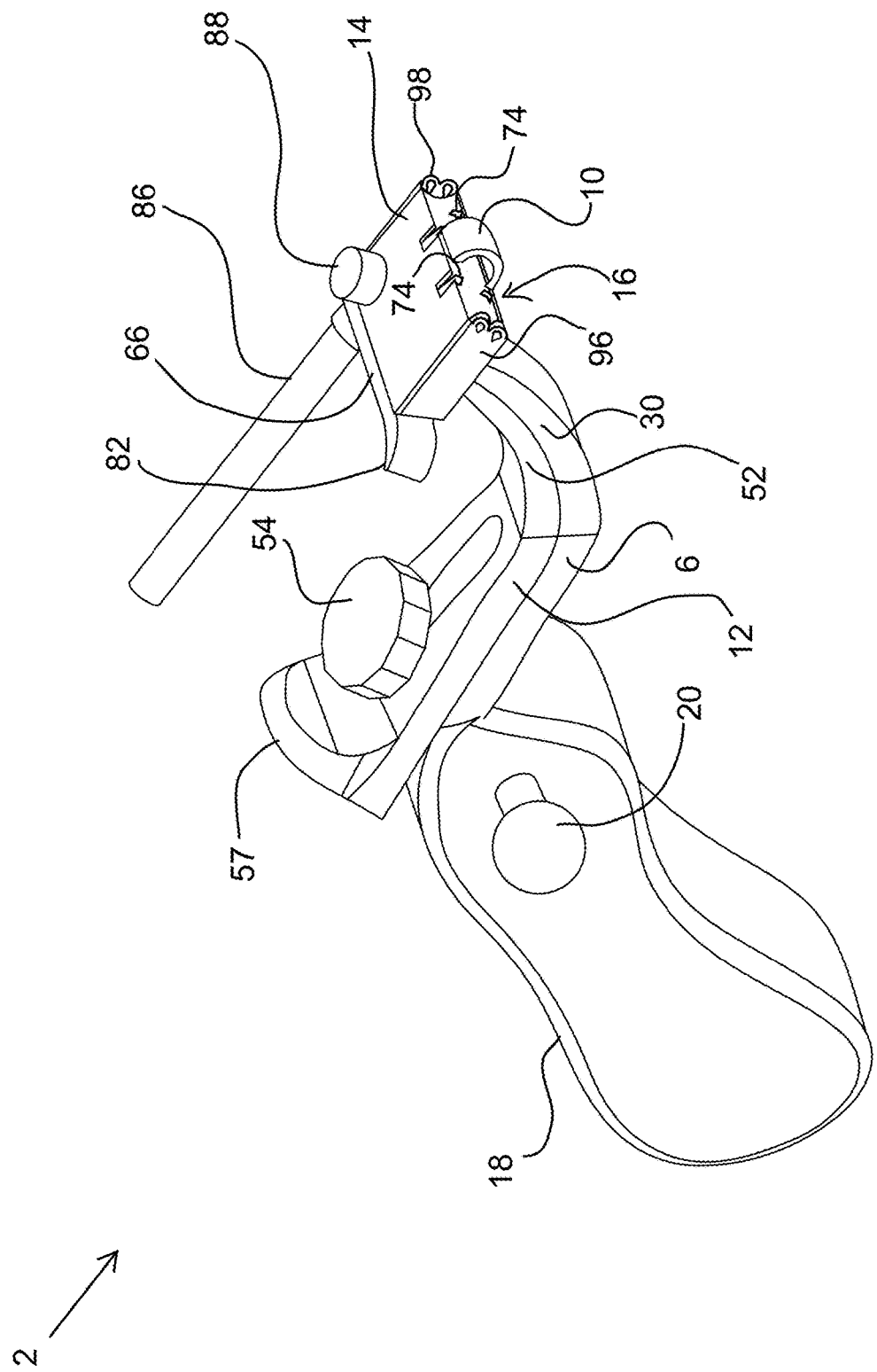
FIG. 3 is an isomeric view of the bone surgery tool in FIG. 1 with the adjustable bracing and surgical surface removed for clarity.
Figure 4:
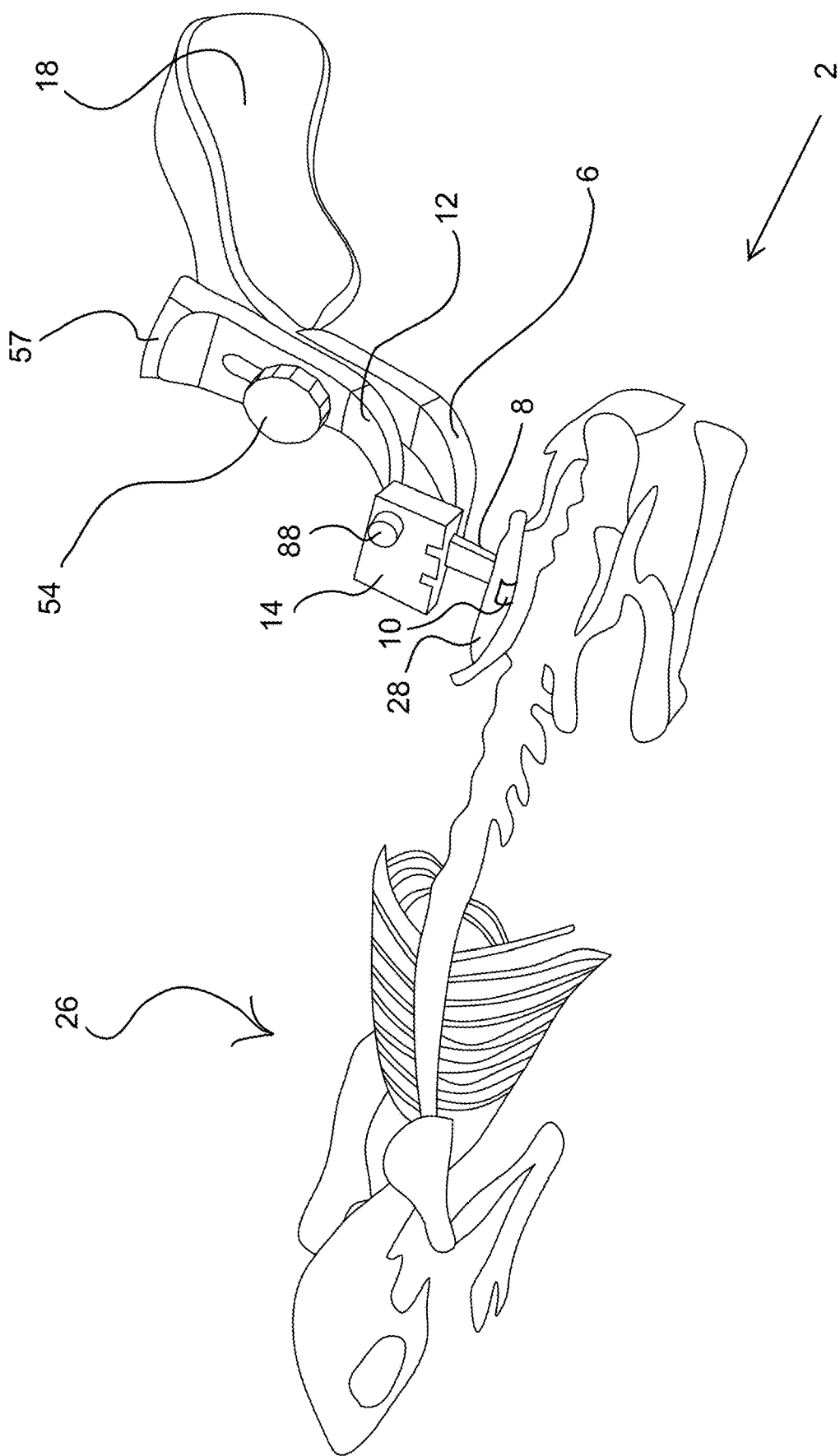
FIG. 4 is an isomeric view of the bone surgery tool in FIG. 3 being used on a mouse skeleton, with the bone surgery tool in a disengaged position.
Figure 5:
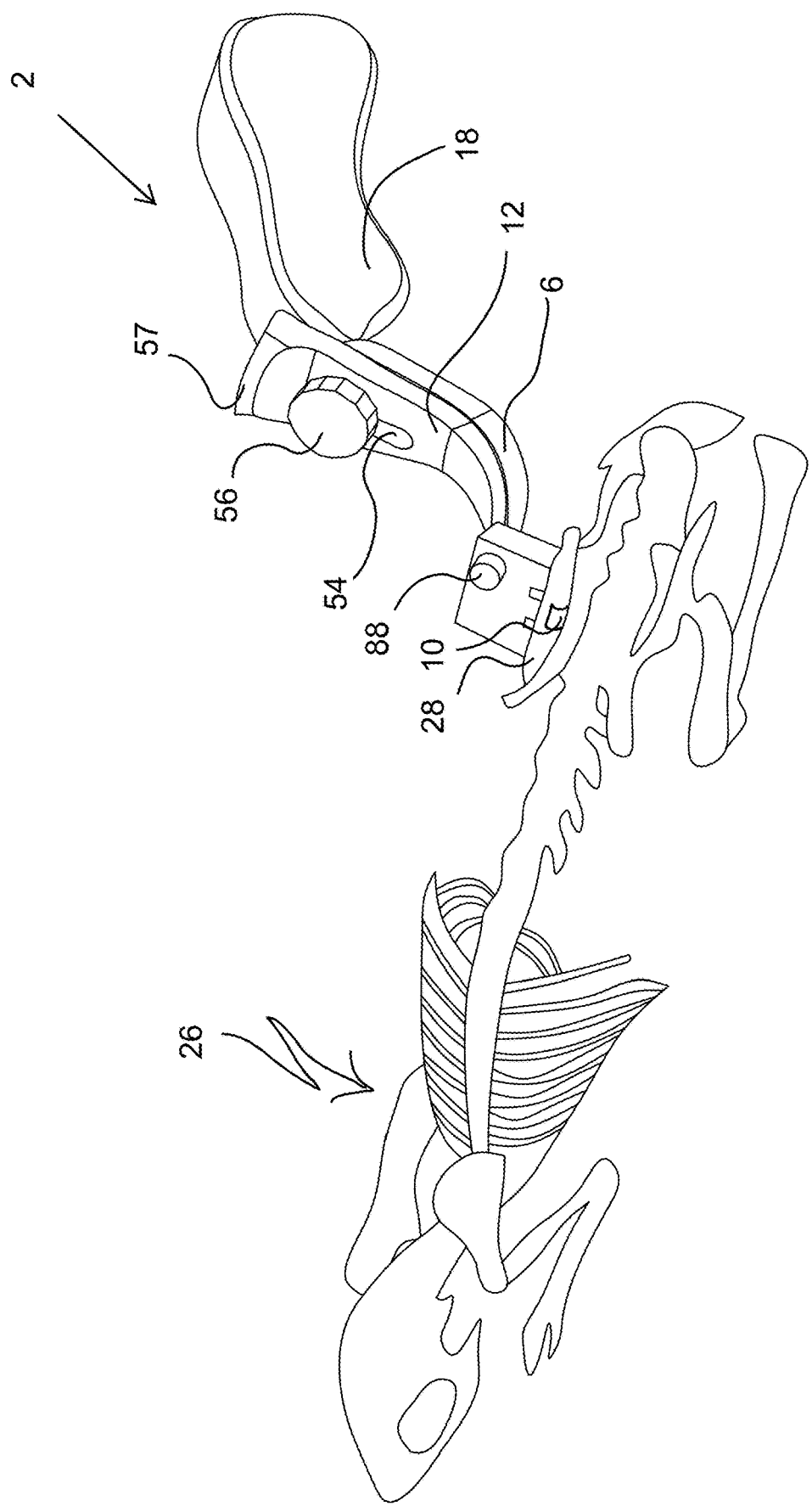
FIG. 5 is an isomeric view of the bone surgery tool in FIG. 3 being used on a mouse skeleton, with the bone surgery tool in an engaged position.
Figure 6:
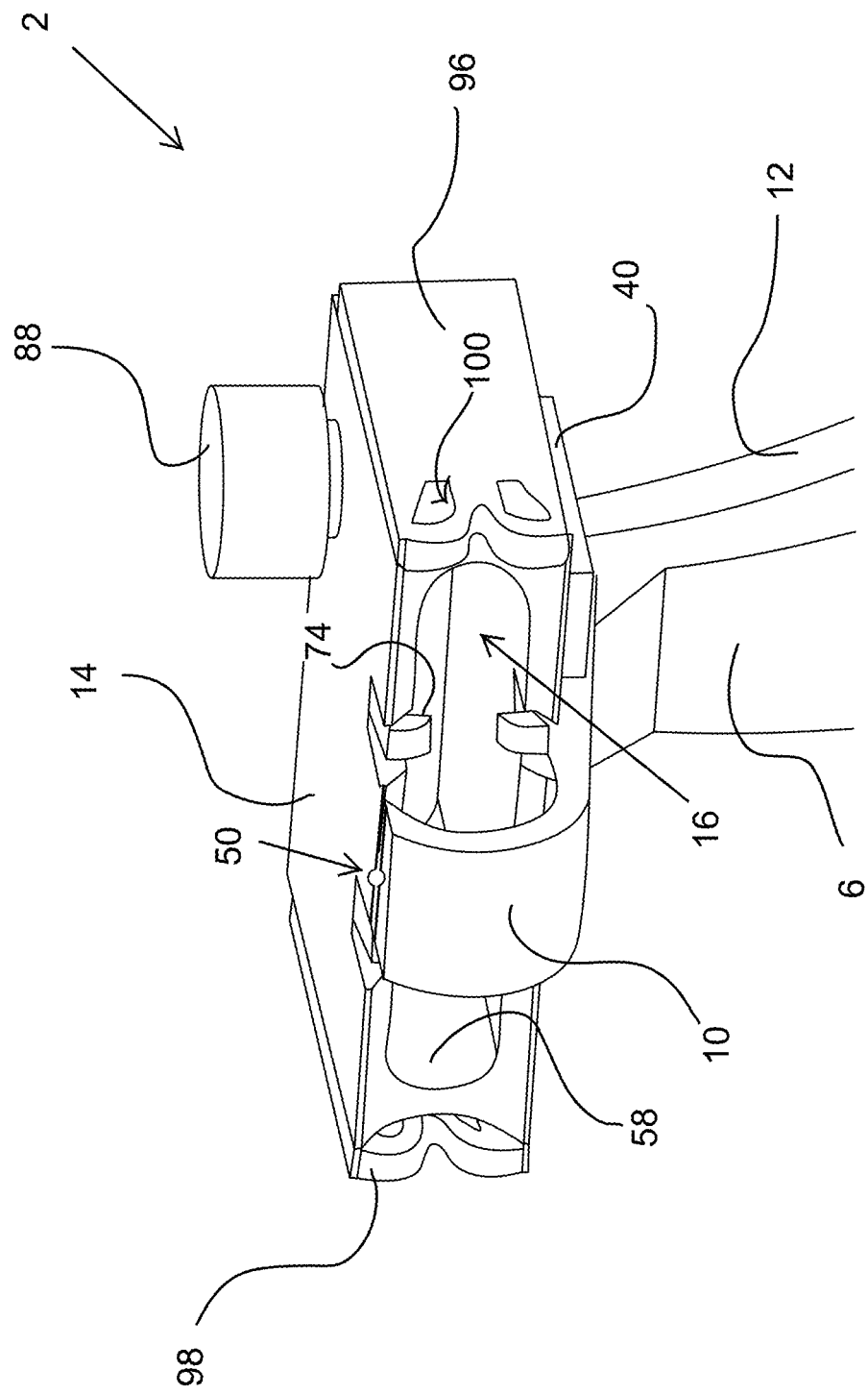
FIG. 6 is an up-close isomeric view of the upper portion of the sliding arm and the fixed arm of the bone surgery tool in FIG. 1.
Figure 7:
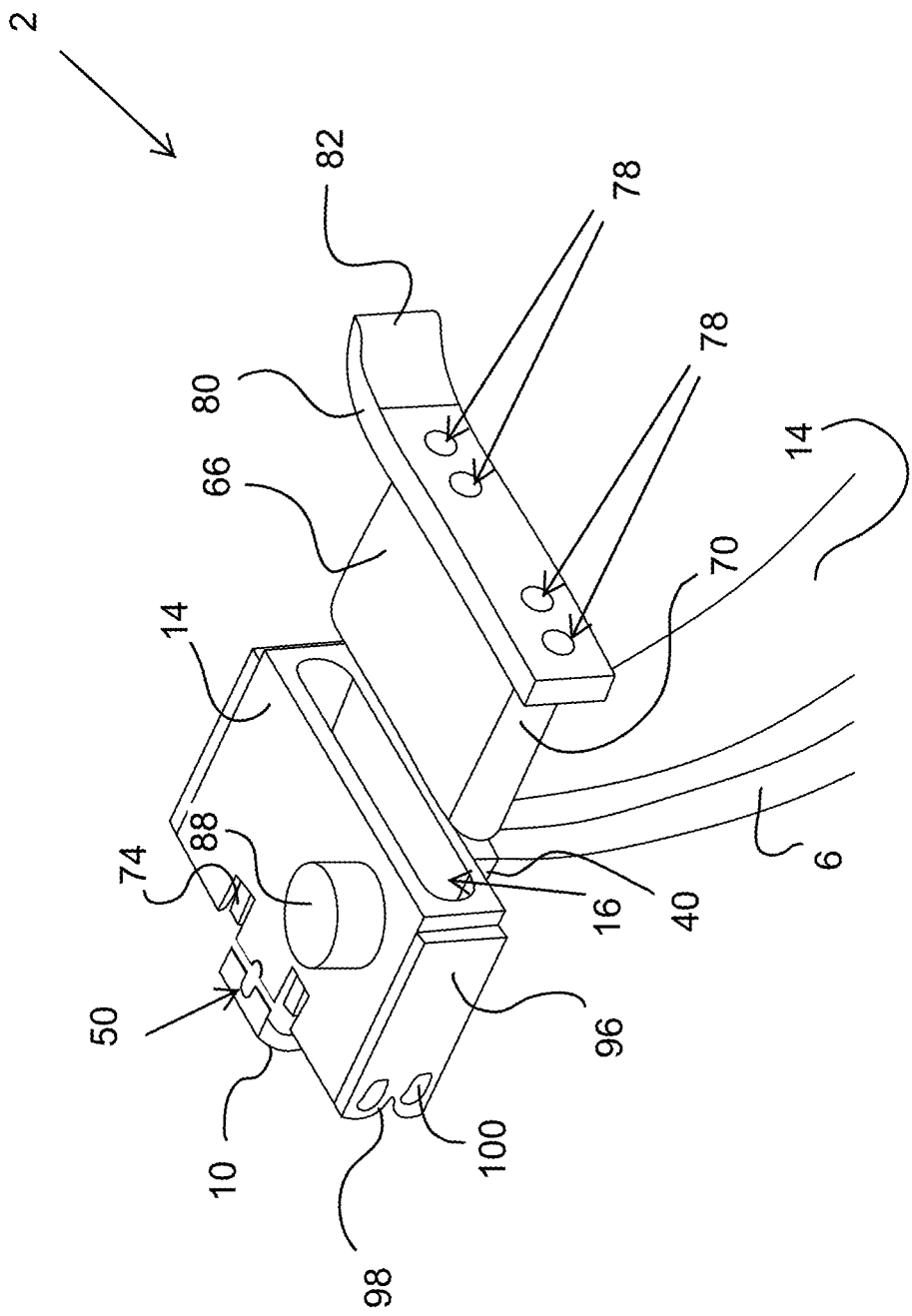
FIG. 7 is an up-close isomeric view of the bone surgery tool in FIG. 6 showing the cartridge aligned for insertion into the slot of the head.
Figure 8:
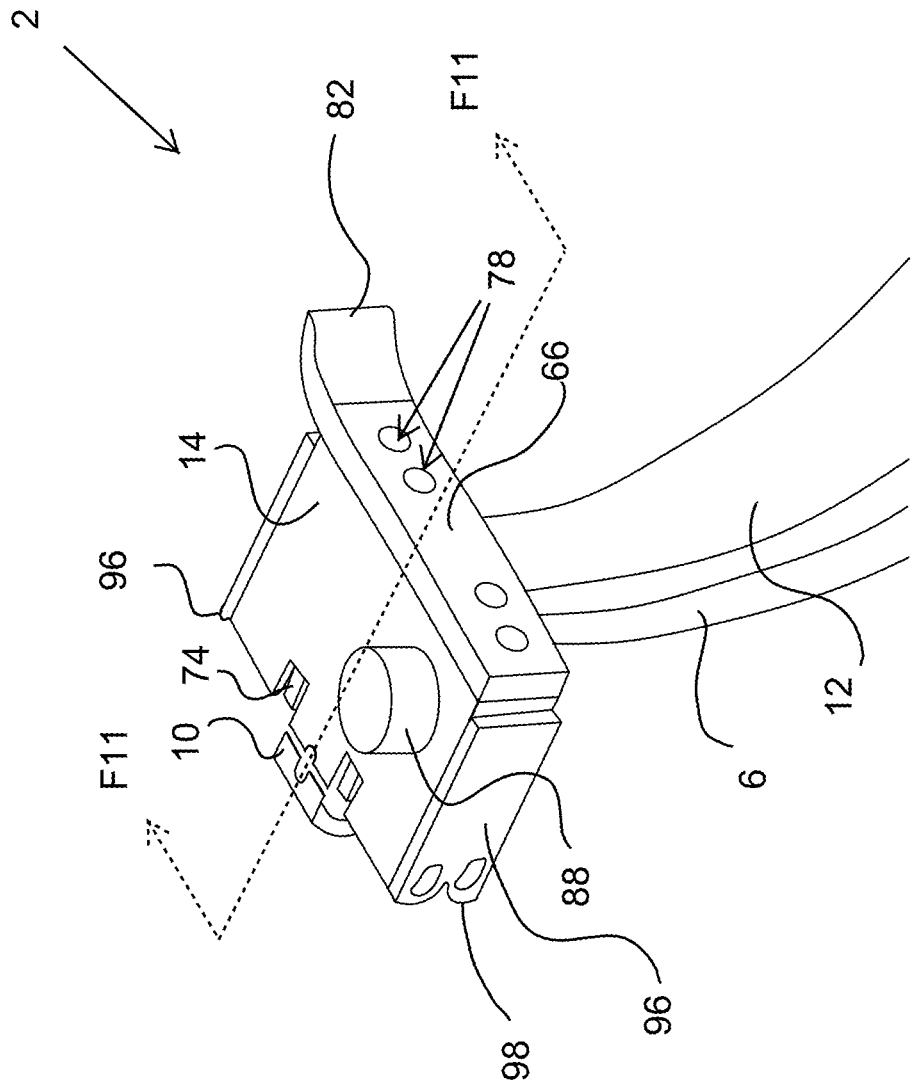
FIG. 8 is an up-close isomeric view of the bone surgery tool in FIG. 7 with an implant and the cartridge inserted into the slot.
Figure 9:
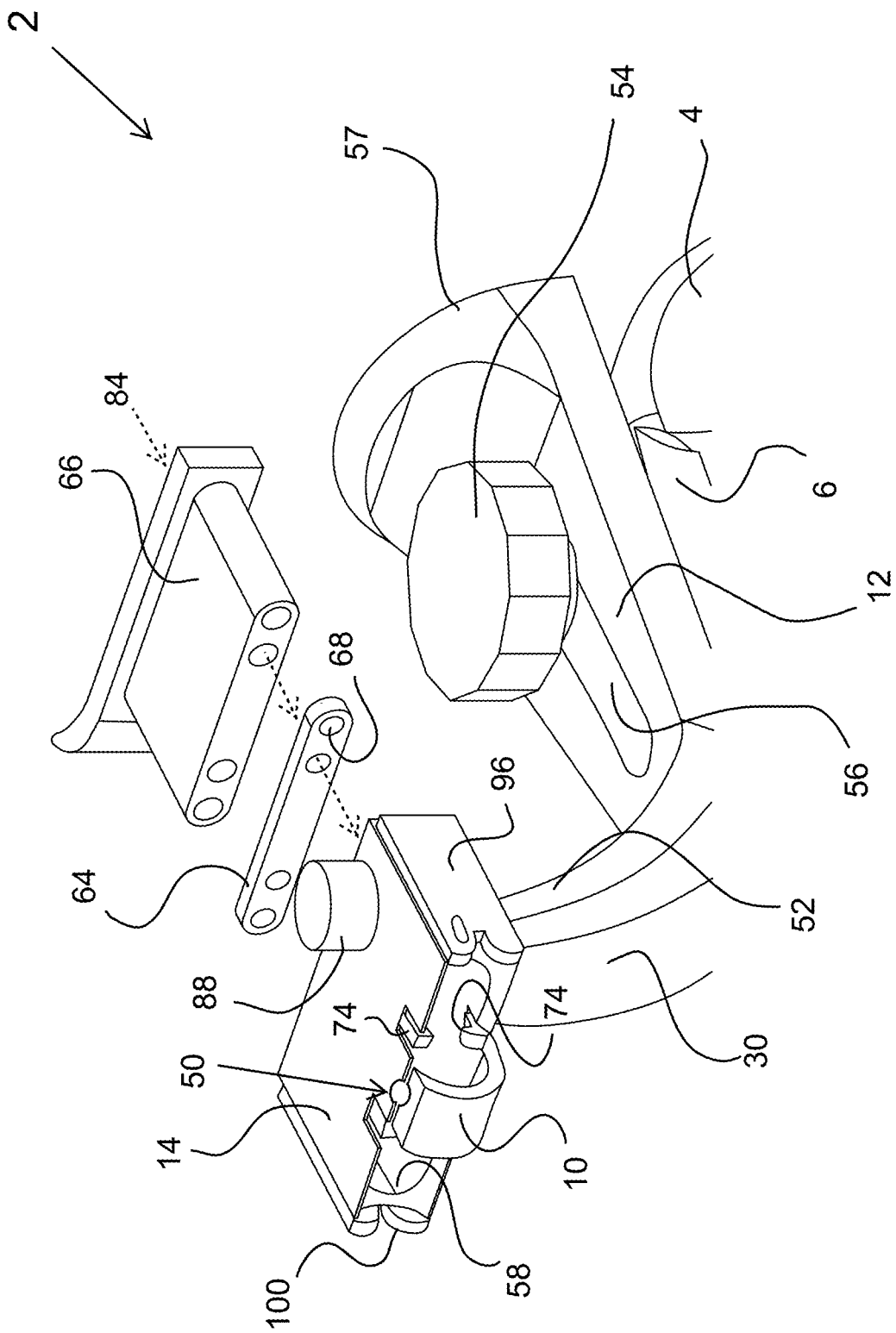
FIG. 9 is a partial exploded view of the bone surgery tool in FIG. 1.
Figure 10:
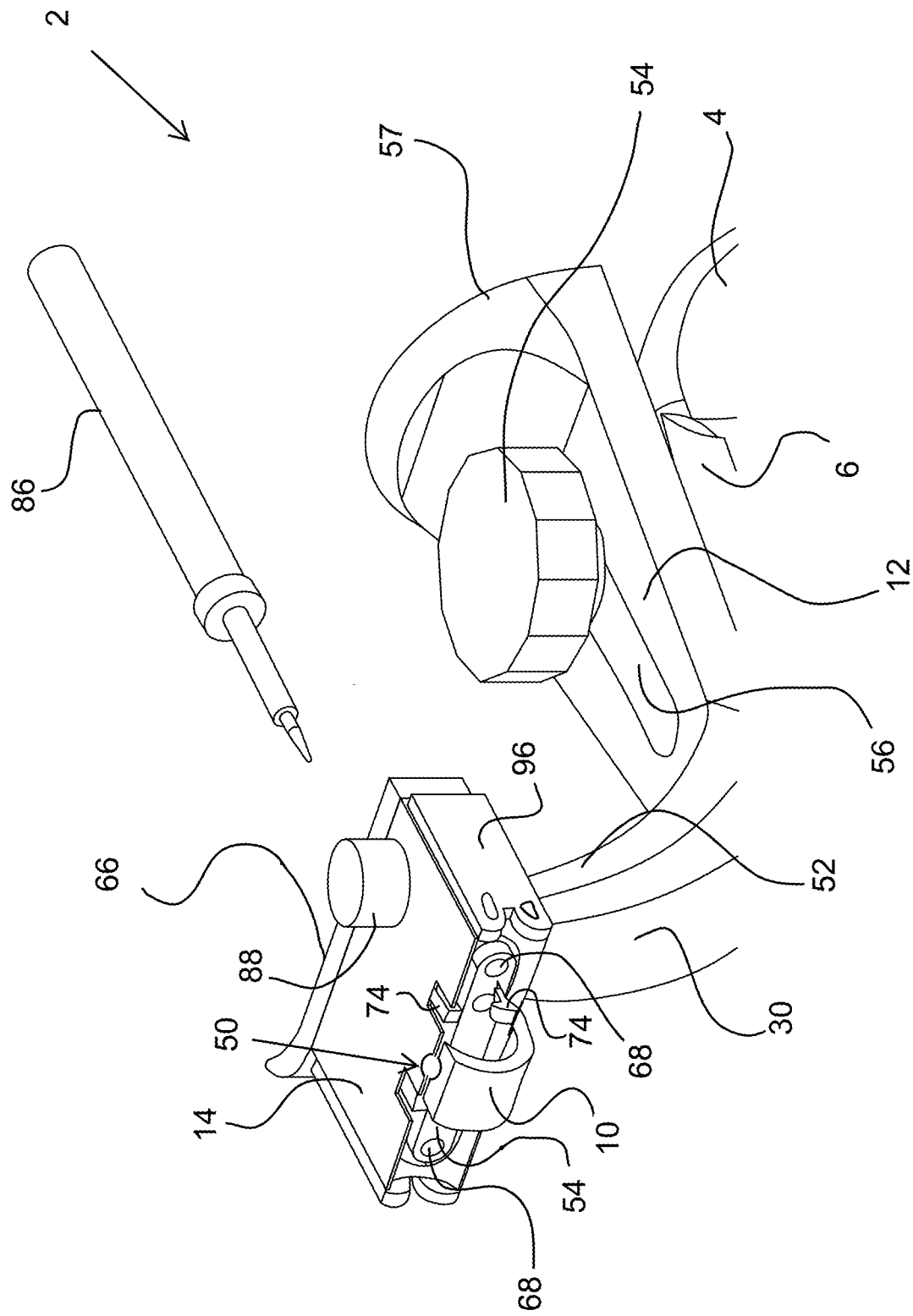
FIG. 10 is an isomeric view of the bone surgery tool in FIG. 9 with the cartridge and implant inserted into the slot and the cartridge lock screwed securely, and a drill or screw driver aligned to work.
Figure 11:
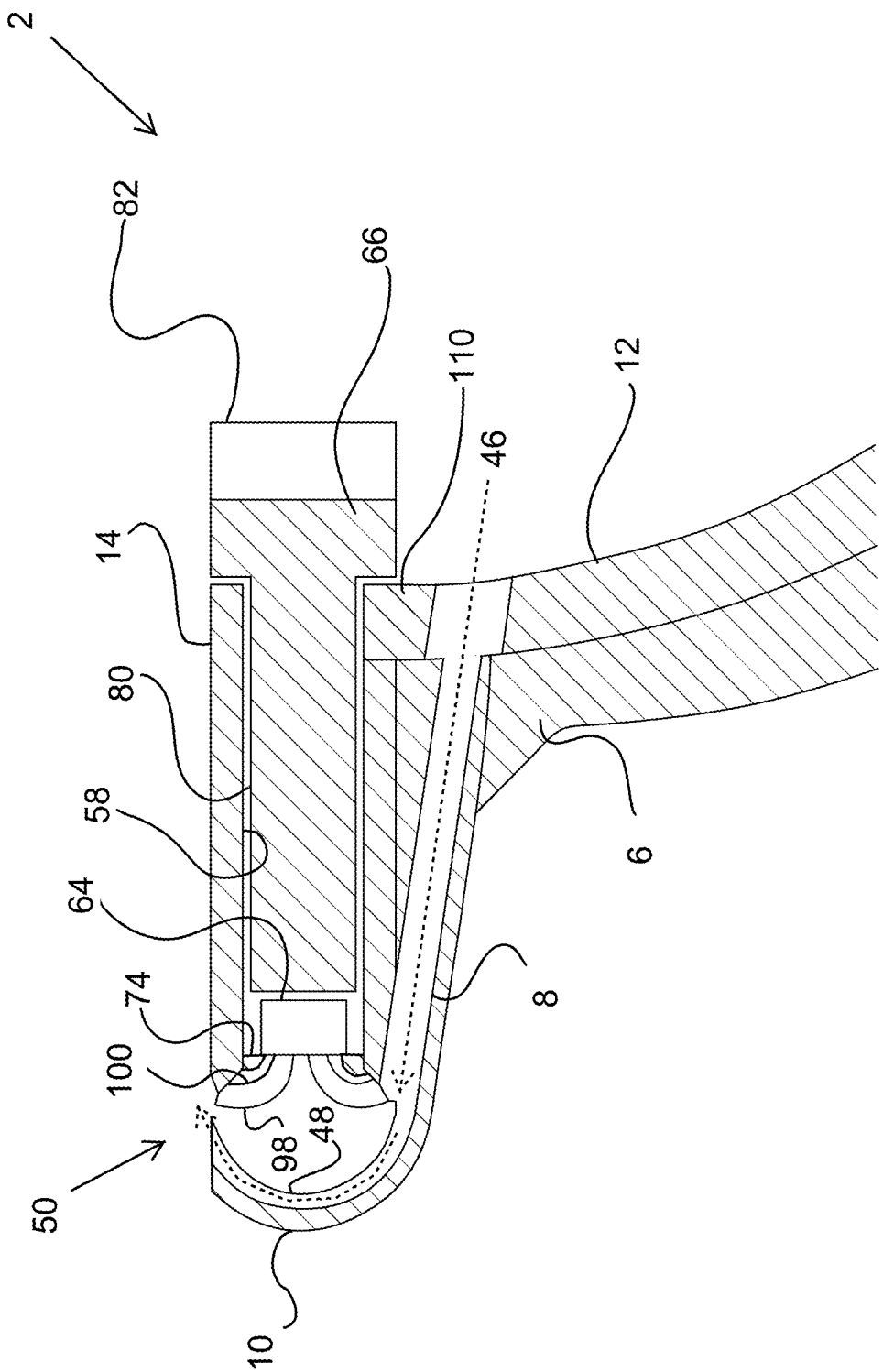
FIG. 11 is a sectional view of the bone surgery tool in FIG. 8 along the sectional line F11 in FIG. 8.
Figure 12:
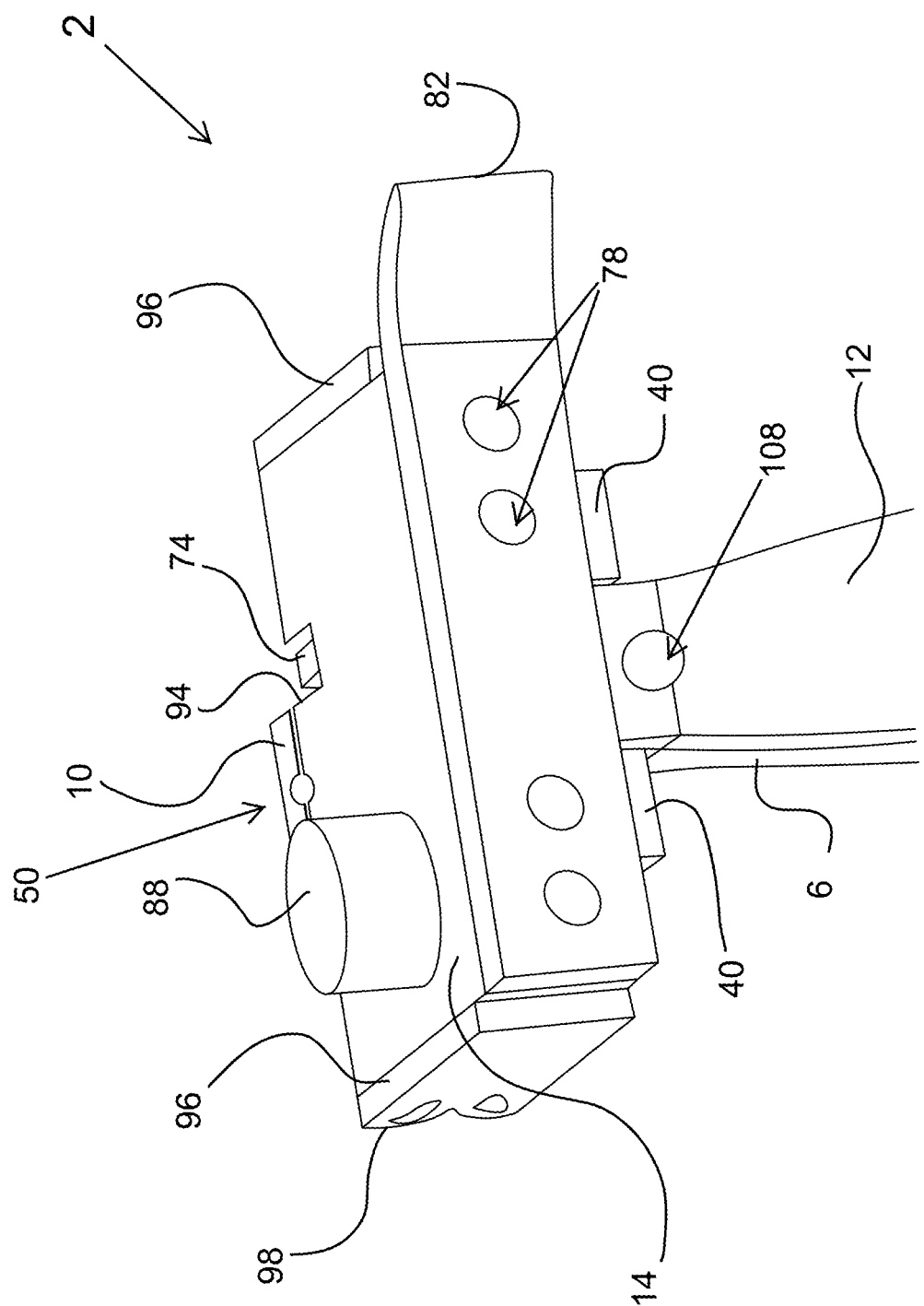
FIG. 12 is an up-close isomeric view of the upper portion of the sliding arm and the fixed arm of the bone surgery tool in FIG. 1.
Figure 13:
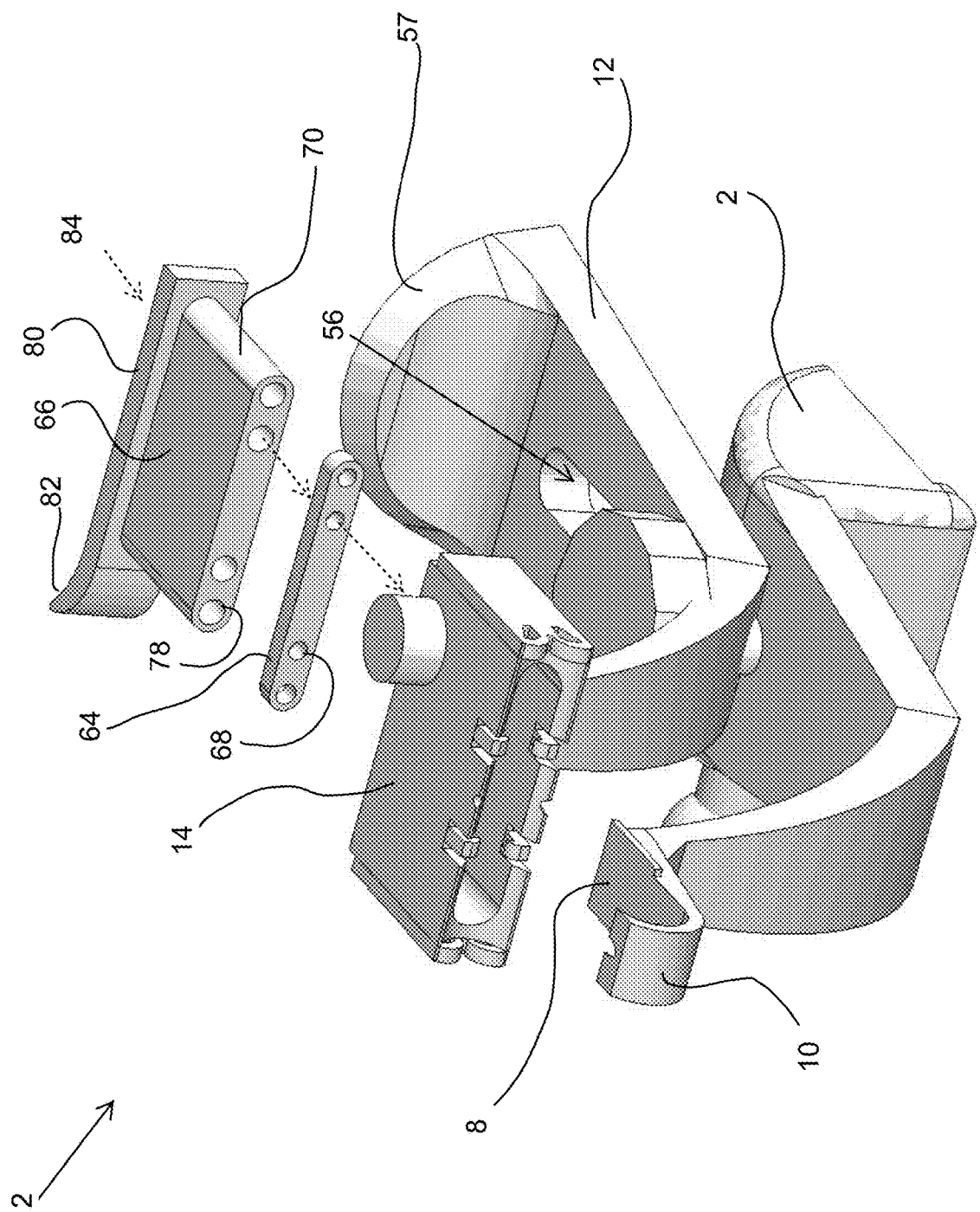
FIG. 13 is a partially exploded isomeric view of the bone surgery tool in FIG. 1 in an over disengaged position, with the handle, adjustable bracing and surgical surface removed for clarity.
Figure 14:
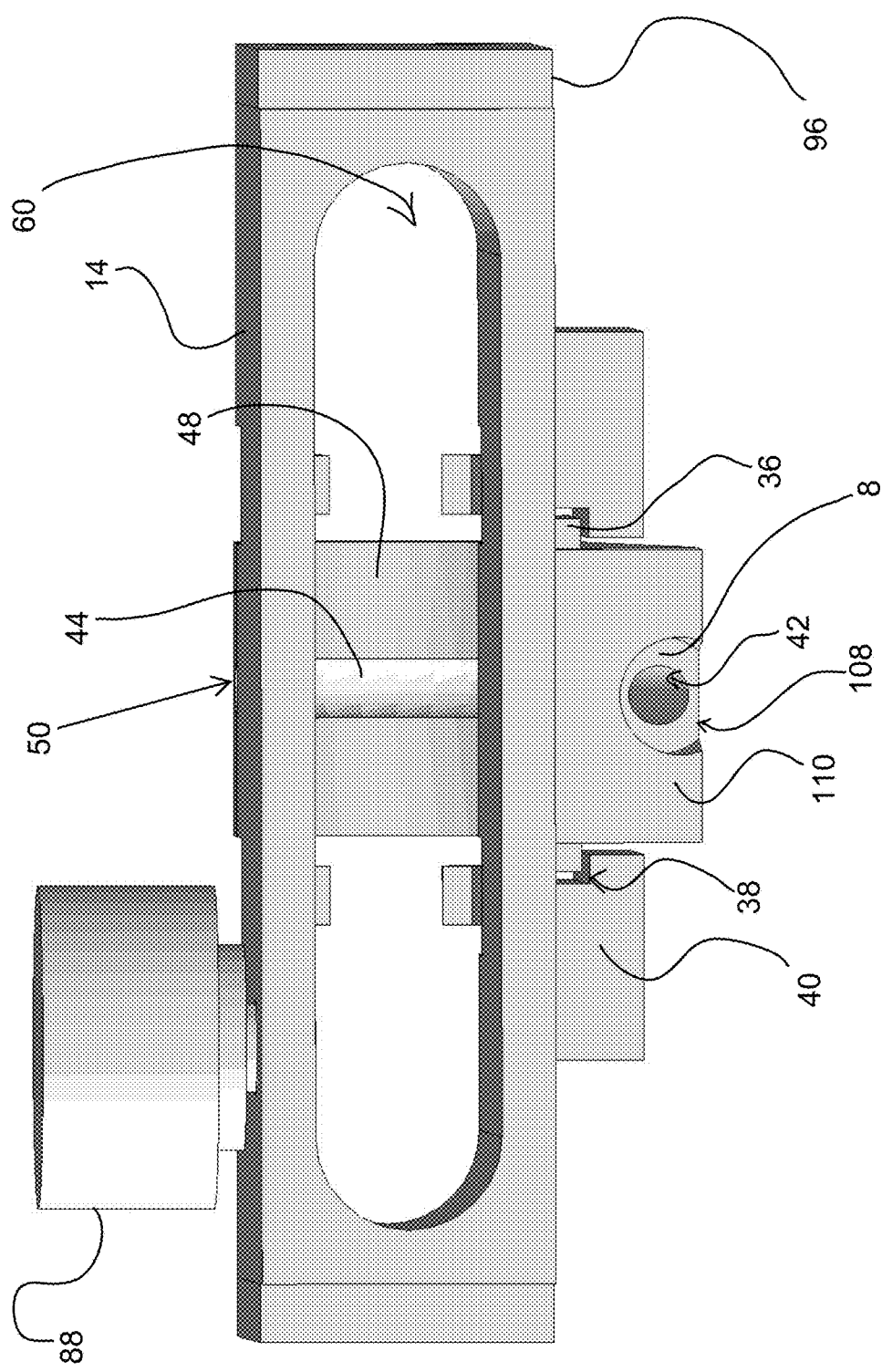
FIG. 14 is a rear isomeric view of the upper portion of the sliding arm and the fixed arm of the bone surgery tool in FIG. 1.
Figure 15:
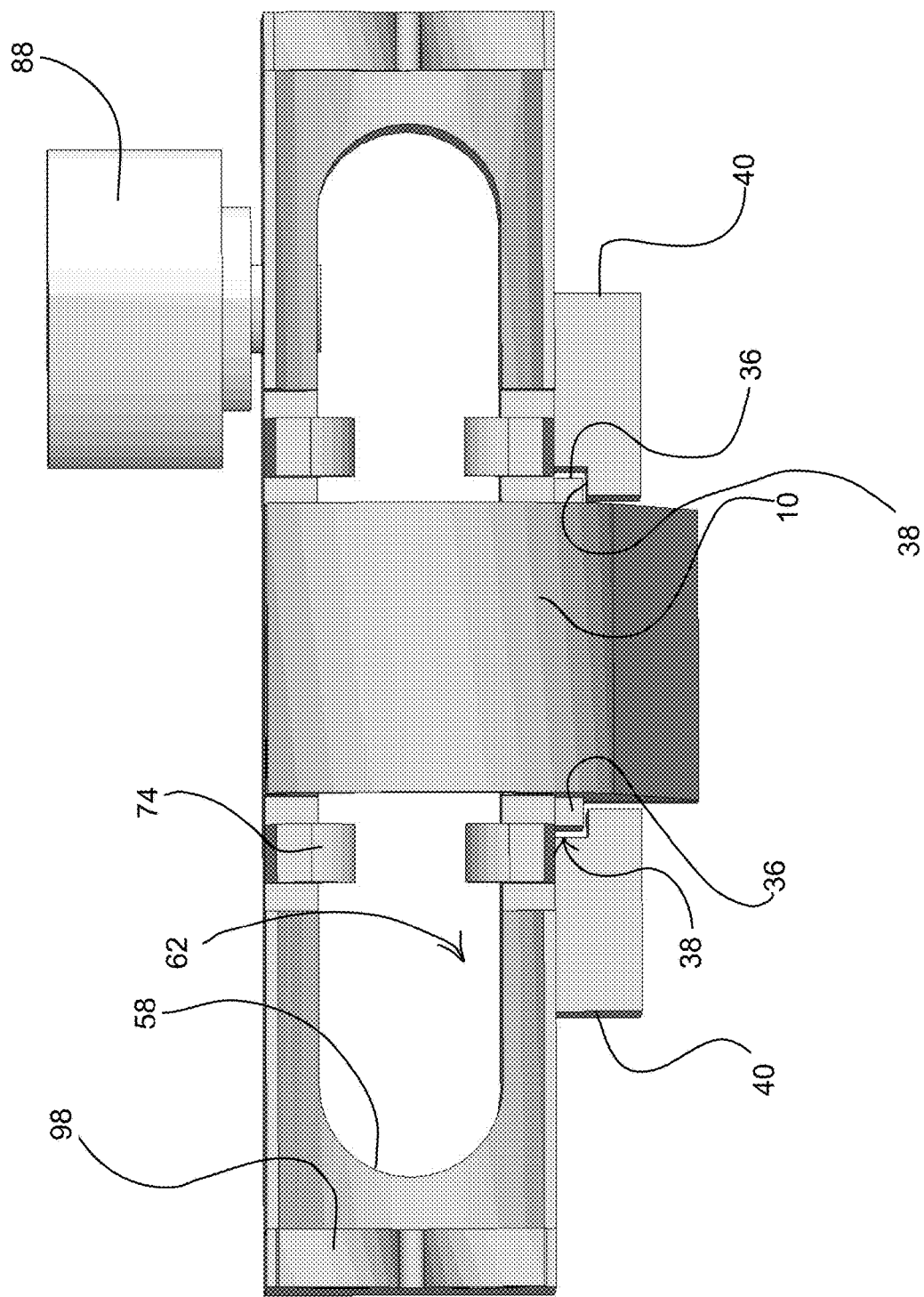
FIG. 15 is a front isomeric view of the upper portion of the sliding arm and the fixed arm of the bone surgery tool in FIG. 14
Figure 16:
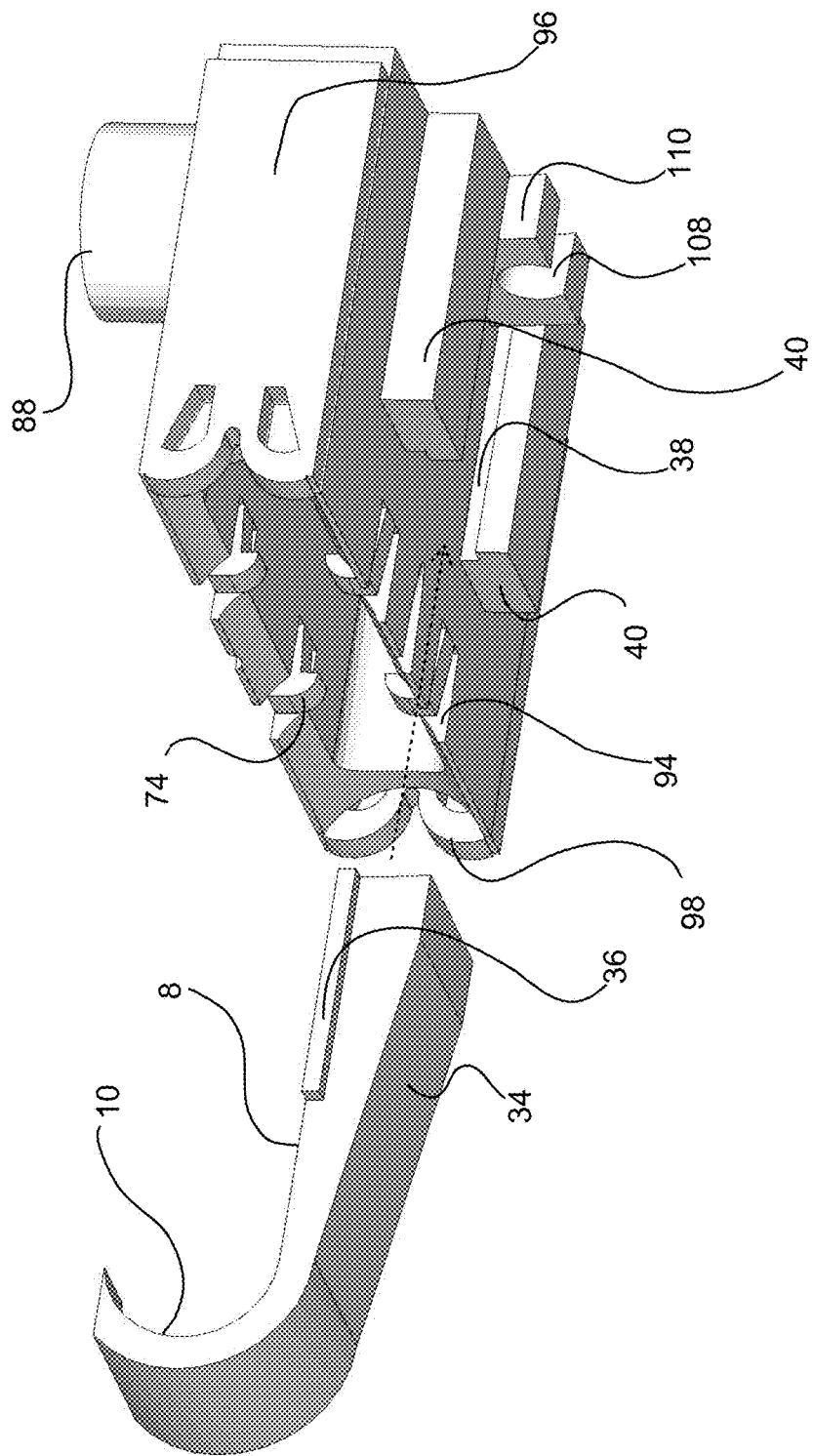
FIG. 16 is an exploded isomeric view of the upper portion of the sliding arm and the fixed arm of the bone surgery tool in FIG. 14.
Figure 17:
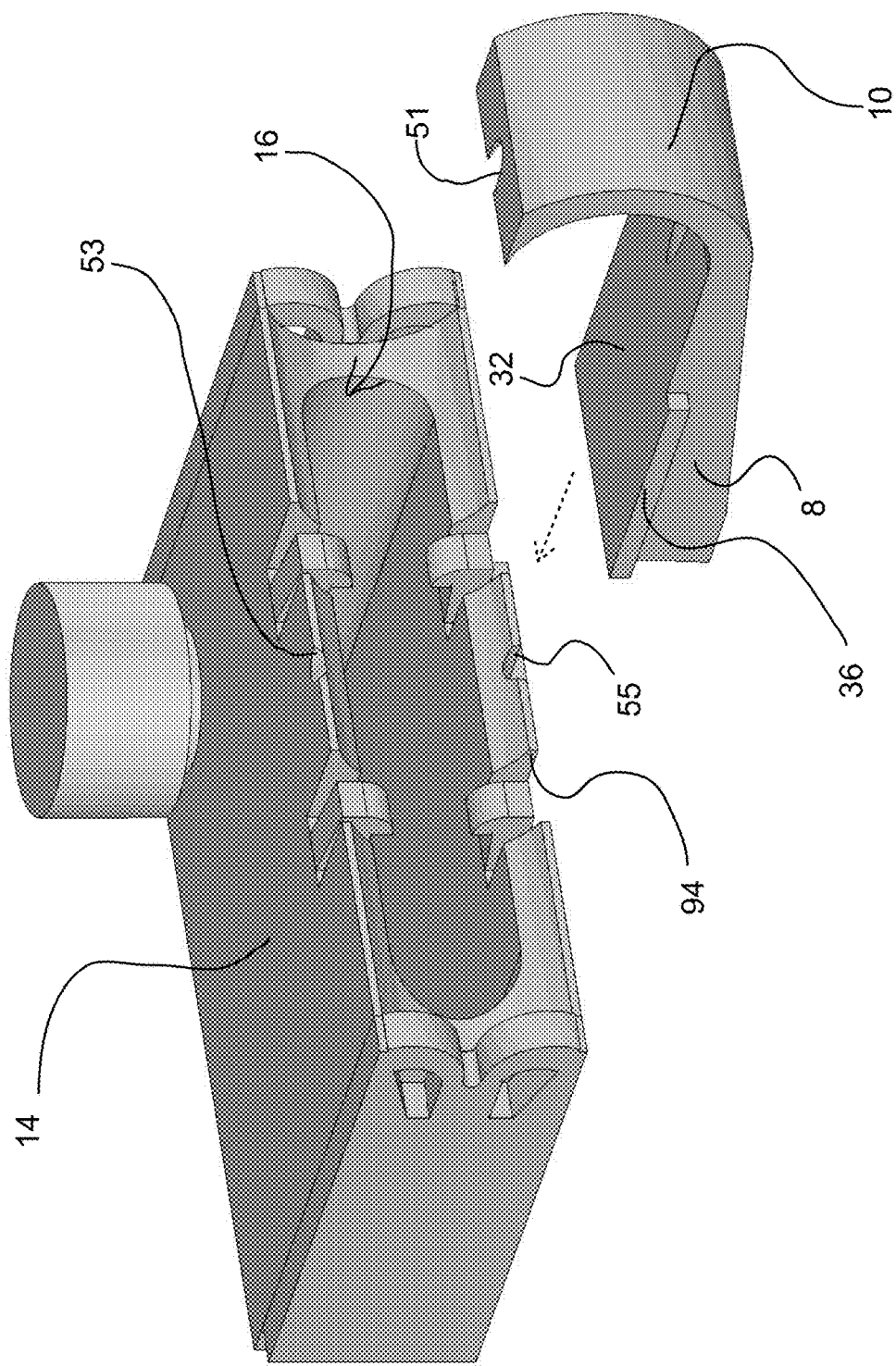
FIG. 17 is an exploded isomeric view of the upper portion of the sliding arm and the fixed arm of the bone surgery tool in FIG. 16.
Figure 18:
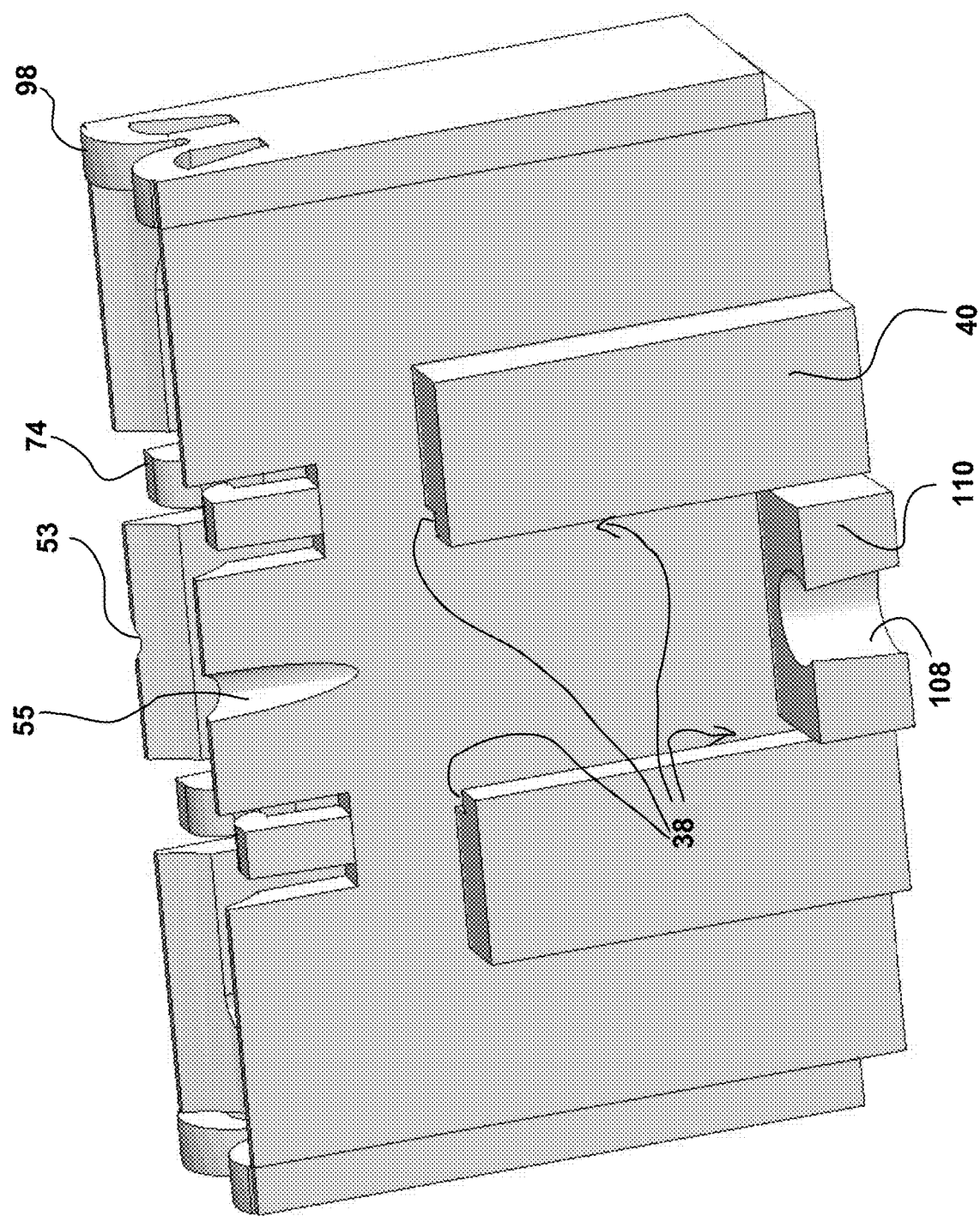
FIG. 18 is a bottom an isomeric view of the upper portion of the fixed arm of the bone surgery tool in FIG. 16.
Figure 19:
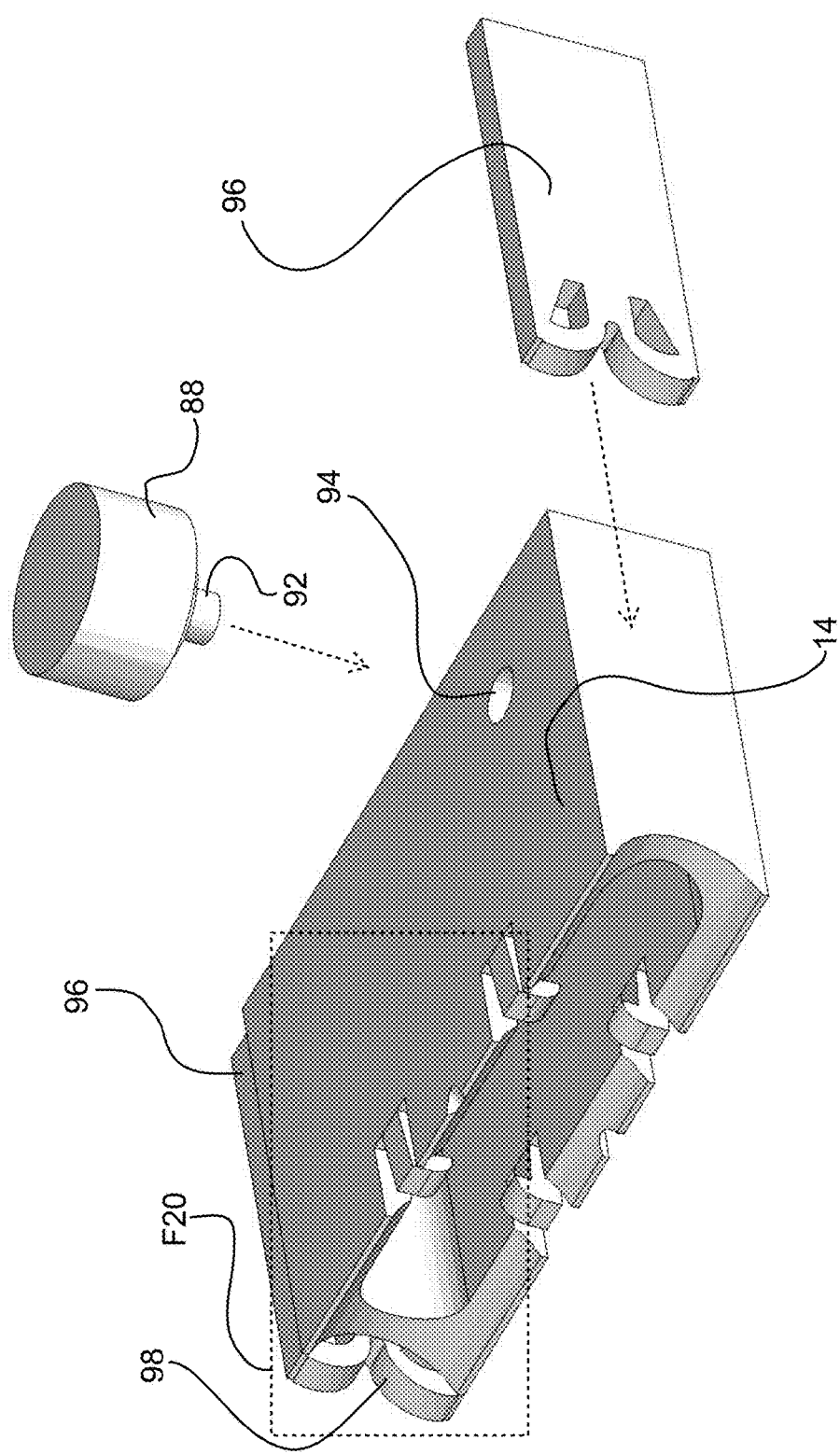
FIG. 19 is a partially exploded isomeric view of the bone surgery tool in FIG. 18.
Figure 20:
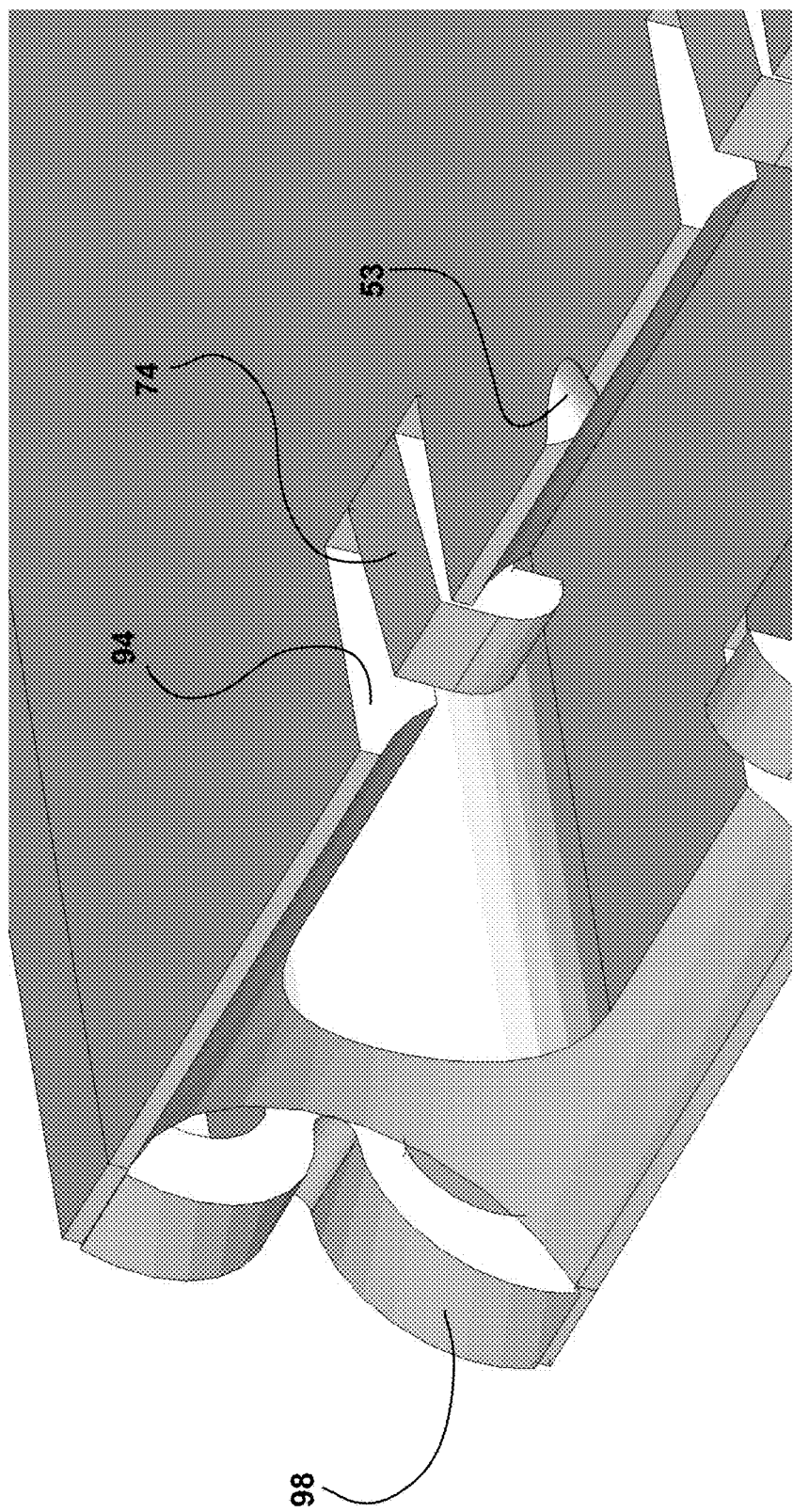

The sliding arm 12 is preferably shaped to slide with a sliding neck portion 52 flush against the fixed neck 30 portion of the fixed arm 6 when the bone surgery tool 2 is in an engaged position (See FIG. 2). This gives increased strength and support for the bone surgery tool 2 when in use. The sliding arm 12 slides forward and backward along a top surface of the rear portion of the fixed arm 6 and around a sliding arm lock 54. The sliding arm lock 54 in this embodiment is a knob screw clamp that extends through a slit path 56 defined in the sliding arm 12 as an elongate through hole. The slit path 56 allows the sliding arm 12 to slide backward to a disengaged position and forward to an engaged position. The knob screw clamp type of sliding arm lock 54, when engaged, frictionally retains the sliding arm 12 in a fixed position relative to the fixed arm 6, and when disengaged, allows the sliding arm 12 to move relative to the fixed arm 6. A helve 57 is preferably provided at a rear portion of the sliding arm 12 and preferably unitarily constructed with the sliding arm 12. The helve has a ridge 59 extending preferably substantially perpendicular to path for engagement and disengagement of the sliding arm 12, and push surface 61 with a relatively large surface area extending perpendicular to the path for engagement and disengagement. The helve 57 is a helpful element that allows the surgeon to easily pull back on the ridge 59 to disengage the sliding arm 12 and make room to fit a bone 28 into the jaw 10, and then push in the push surface 61 to engage the sliding arm 12 and head 14 with the bone 28.

At an upper portion of the sliding arm 12 is a head 14. The head 14 has a in inner wall 58 defining a through cavity or slot 16 with a rear opening 60 and a front opening 62. The slot 16 is shaped obround to receive and selectively retain an implant 64 and a cartridge 66 within the slot 16.

The implant 64 preferably has one or more screw holes 68 disposed on the implant 64 for securing the implant 64 to the bone 28 of the animal 26. In the embodiments shown in FIGS. 9, 10, and 13, for example, the implant 64 is an obround face shaped fixture plate with a rectangular cross section and four drill holes/screw holes 68. In a second embodiment, as shown in FIGS. 27-30, a special cartridge 66 may be used for smaller implants 64, with, for example, two screw holes 68, while using the same sized head 14. In such embodiments, the cartridge 66 would have a longer cartridge insert 70 than in the first embodiment, with a leading edge 72 of the cartridge insert 70 reaching to the teeth of the snap retainers 74 at the front opening 62 of the slot 16, but with an implant recess 76 also. The implant recess 76 would be shaped like the implant 64 being used with the special cartridge and the implant recess 76 would have the depth of the implant 64. In this manner, by using special cartridges 66, a single head 14 can function with a variety of different sized implants 64.

The cartridges 66 include a cartridge insert 70, one or more cartridge bores 78, and preferably a cartridge collar 80 and a cartridge hilt 82. The cartridge bores 78, together with the screw holes 68, define a drill passageway 84 and provide access for a drill 86 to drill pilot holes into the bone 28 and a screw driver to screw screws into the bone 28, thereby affixing the implant 64 to the bone 28. The cartridge collar 80 controls how far into the slot 16 the cartridge insert 70 travels, and prevents the cartridge 66 from being over inserted. The hilt 82 provides a grip to grasp to more easily remove the cartridge 66 from the slot 16 when desired, such as when the operation is complete.

In order to secure the cartridge 66 in place once it is fully inserted into the slot 16 from the rear opening 60, and the cartridge collar 80 is flush against the head 14 at the rear opening 60, a cartridge lock 88 is engaged, releasably retaining the cartridge 66 in place in the slot 16. The cartridge lock 88 in the embodiment shown is a knob screw clamp with a threaded shaft 90 that extends through a threaded port 92 in the head 14. When the cartridge lock 88 is disengaged (unscrewed in this instance), the threaded shaft 90 is spaced from the cartridge insert 70, allowing the cartridge 66 to be moved in and out of the slot 16 of the head 14. When the cartridge lock 88 is engaged (screwed-in in this instance), the threaded shaft 90 applies pressure on the cartridge insert 70, frictionally retaining the cartridge 66 in place in the slot 16. When the cartridge lock 88 is engaged, it creates a moment of force on the head 14, and potential deformation, which the tracks 36, channels 38, and blocks 40 help to mitigate.

On a front portion of the head 14 is preferably a plurality of snap retainers 74 extending inward from the perimeter of the head 14, coincident with a respective notch 94 in the edge of the head 14. In further embodiments, the snap retainers 74 could just be recessed in indentations in the inner wall 58 of the head 14. The snap retainers 74 may be of unitary construction with the head 14. The snap retainers 74 provide a releasable forward barrier for the implant 64 when the implant 64 is loaded in the slot 16. Once the implant 64 is screwed into or otherwise secured to the bone 28, and the bone 28 and the head 14 are moved apart relative to on another, the forward force on the implant 64 is more than sufficient to cause the snap retainers 74 to pivot outward in the notch 94 and allow the implant 64 to exit the front opening 62 of the slot 16.

Figure 21:
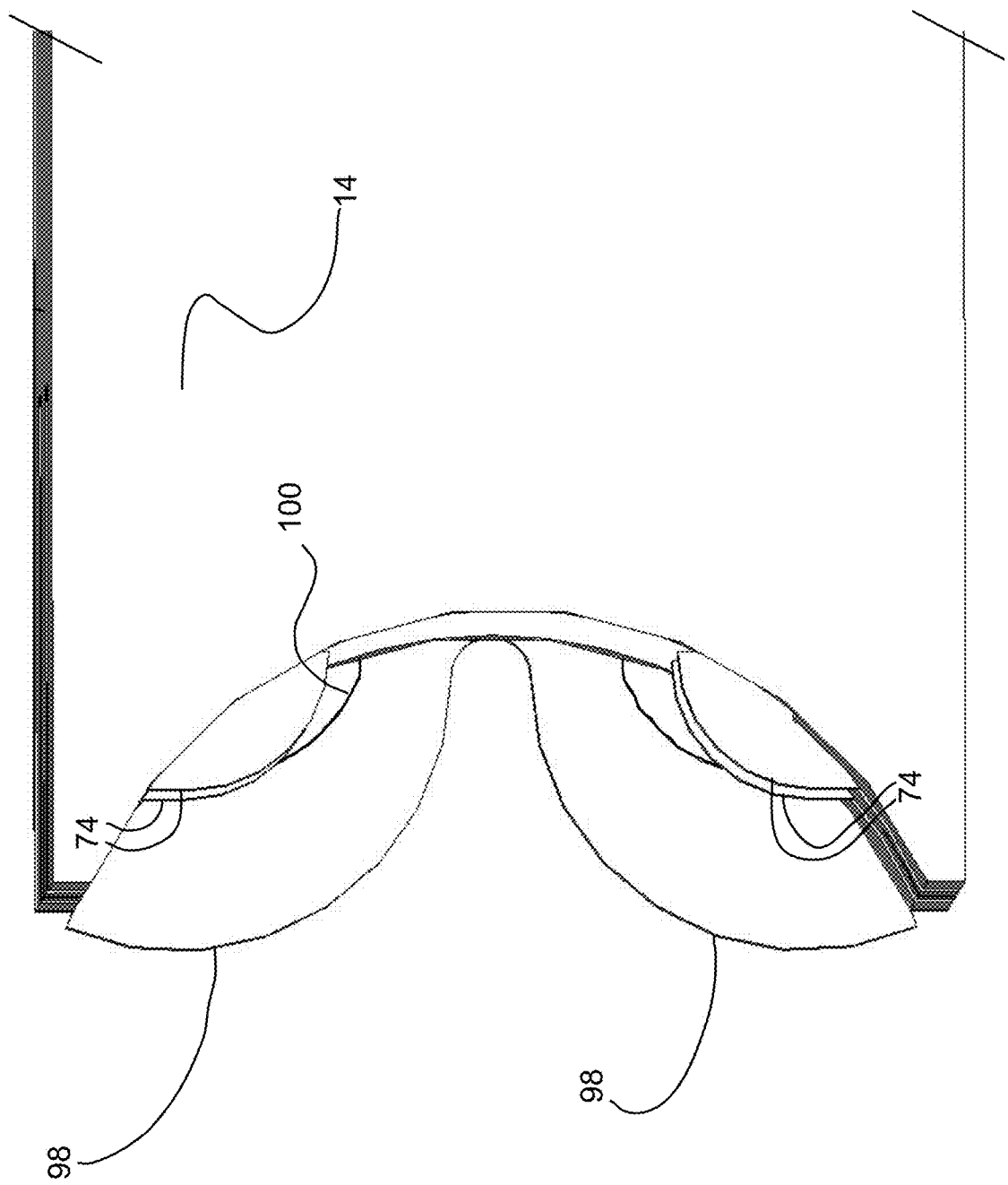
FIG. 21 is a partial side plan view of the bone surgery tool in FIG. 19.
Figure 22:
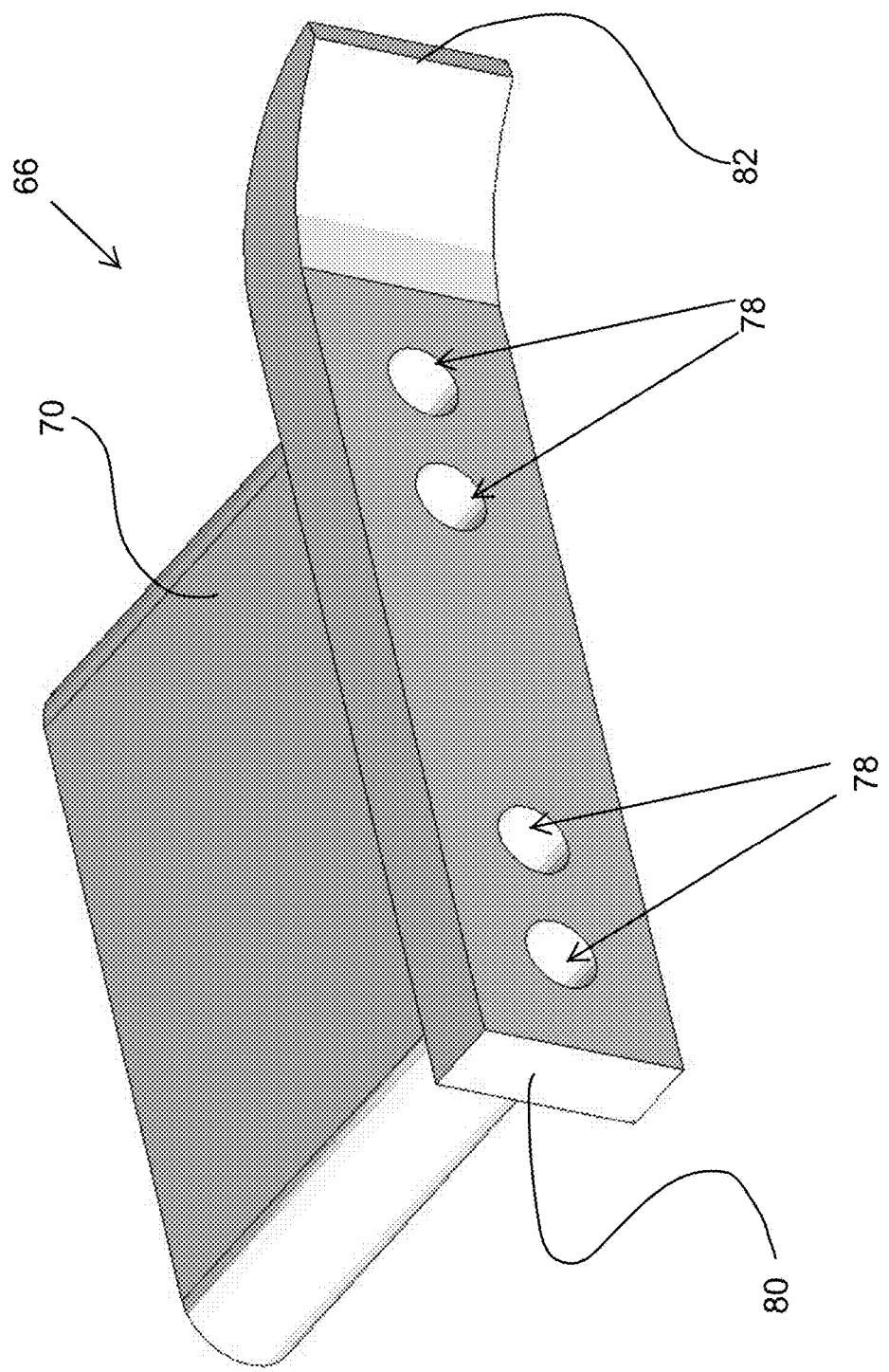
FIG. 22 is an isomeric view of the cartridge in FIG. 1.
Figure 23:
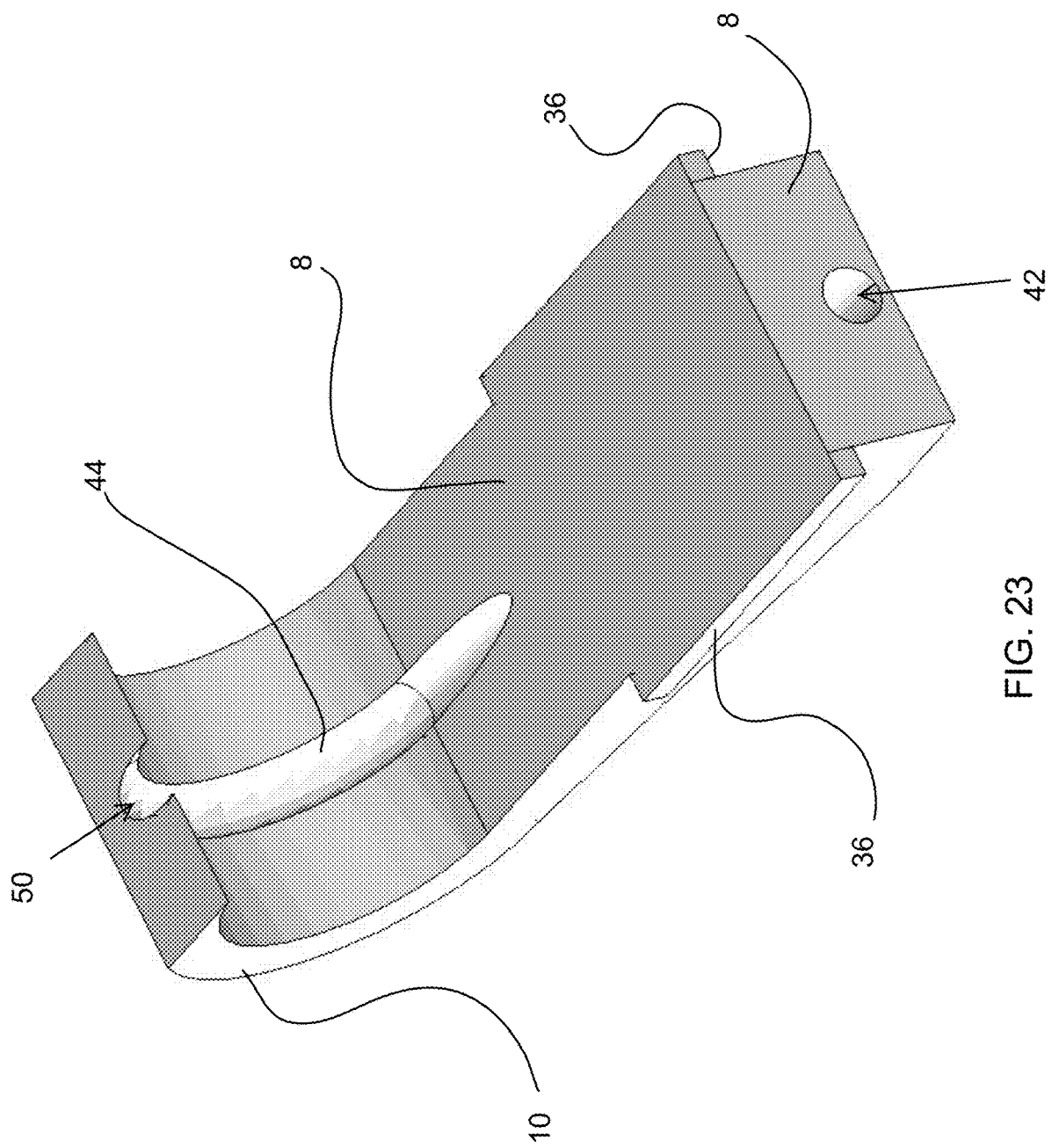
FIG. 23 is an isomeric view of the upper portion of the sliding arm of the bone surgery tool in FIG. 16.
Figure 24:
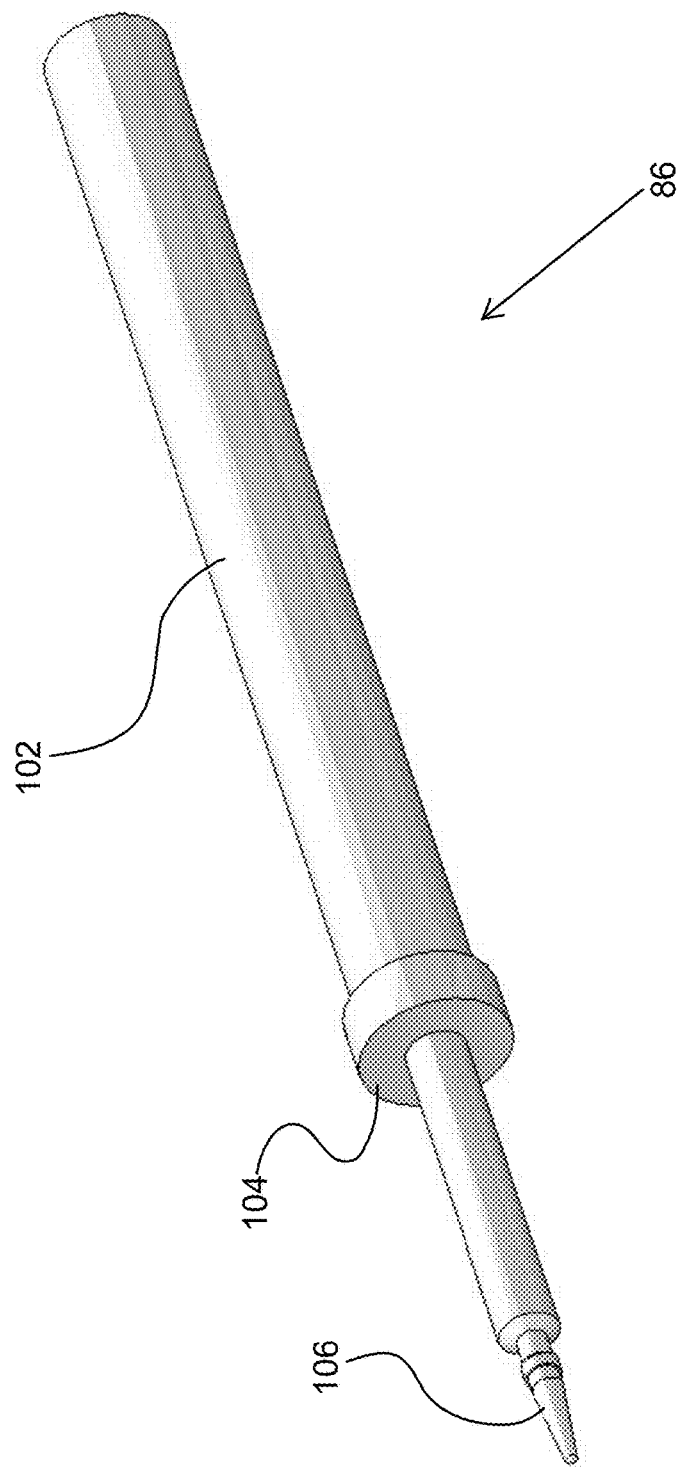
FIG. 24 is an isomeric view of the drill in FIG. 1.
Figure 25:
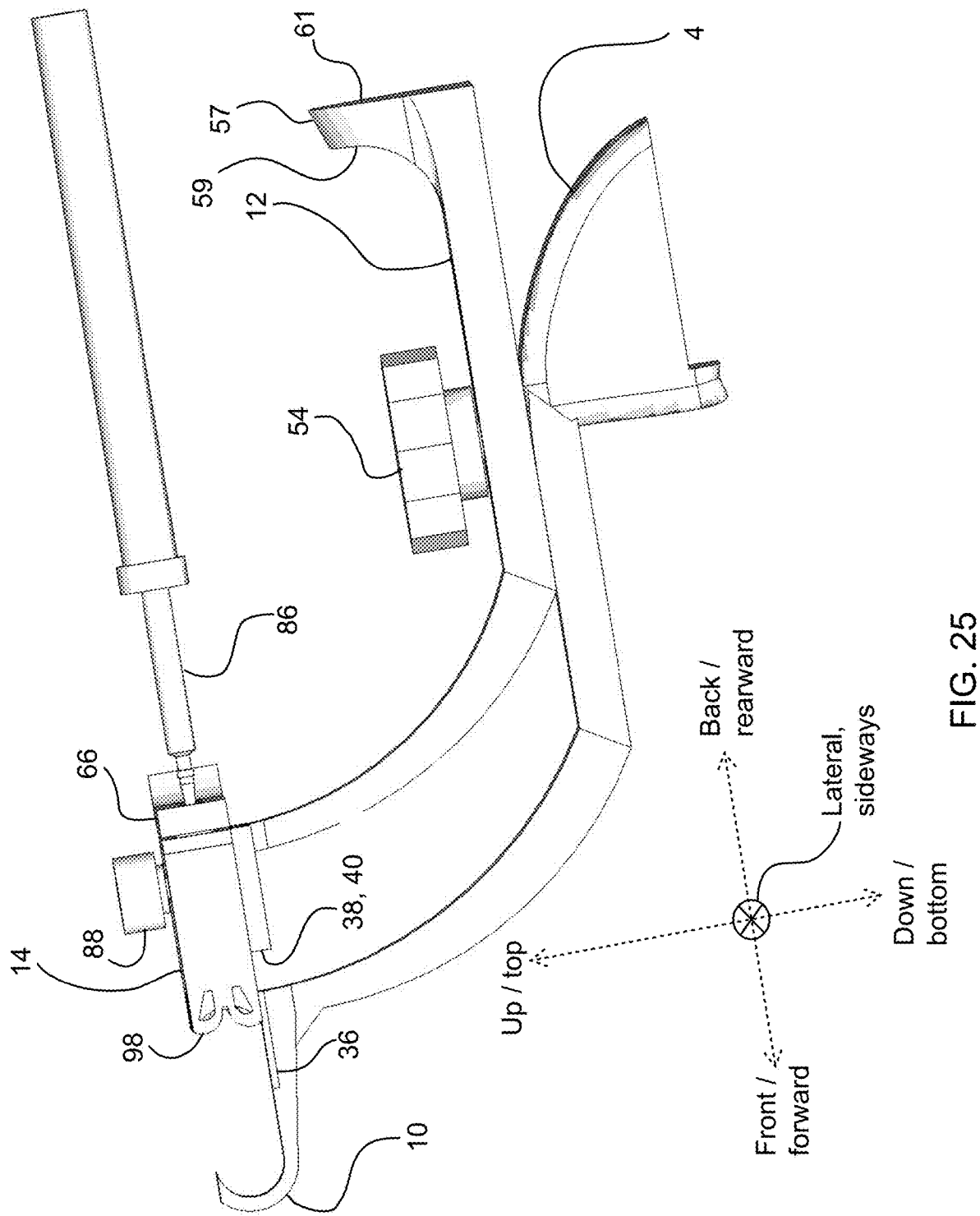
FIG. 25 is an isomeric view of the bone surgery tool in FIG. 1 in a disengaged position, with the handle, adjustable bracing and surgical surface removed for clarity.
Figure 26:
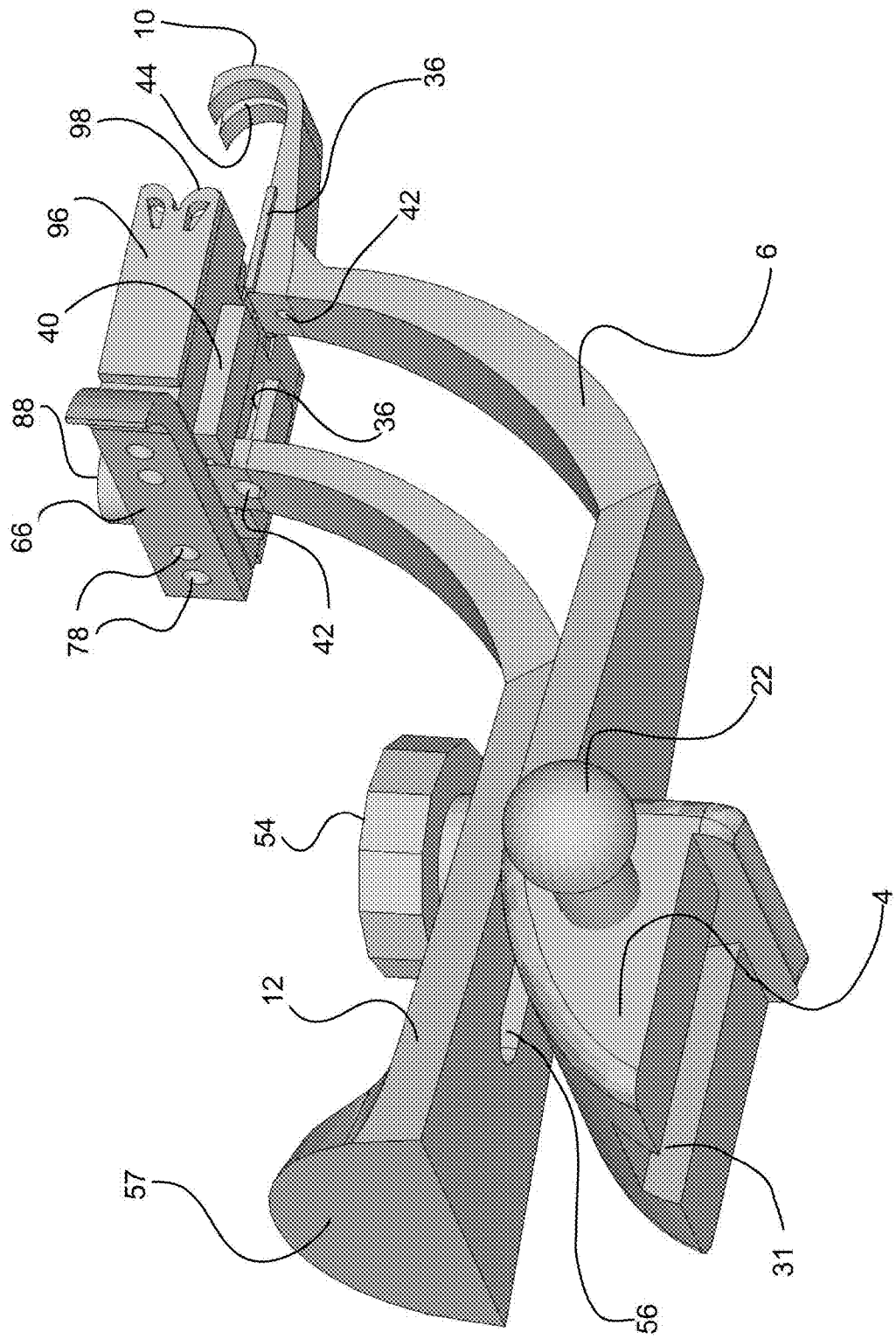
FIG. 26 is an isomeric view of the bone surgery tool in FIG. 25.
Figure 27:
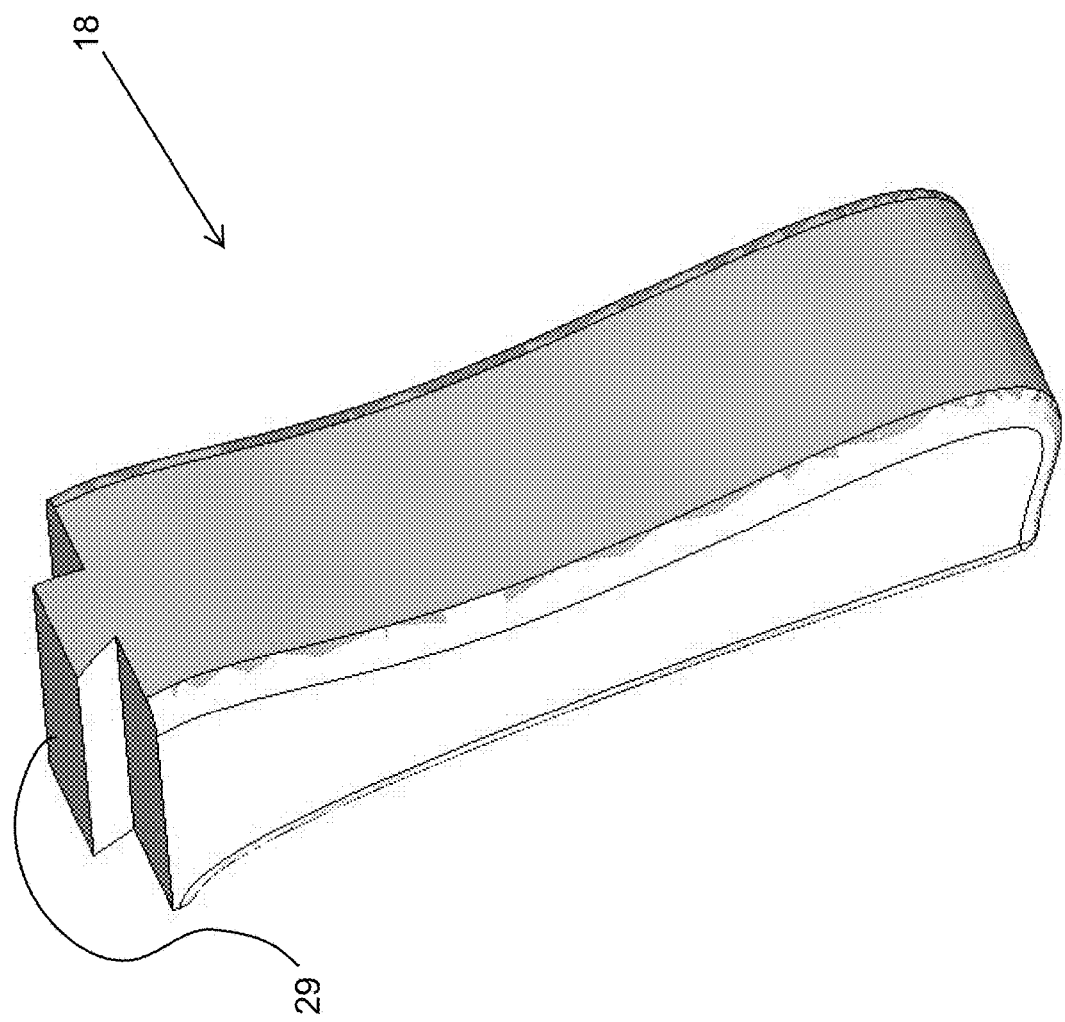
FIG. 27 is an isomeric view of the handle in FIG. 1.
Figure 28:
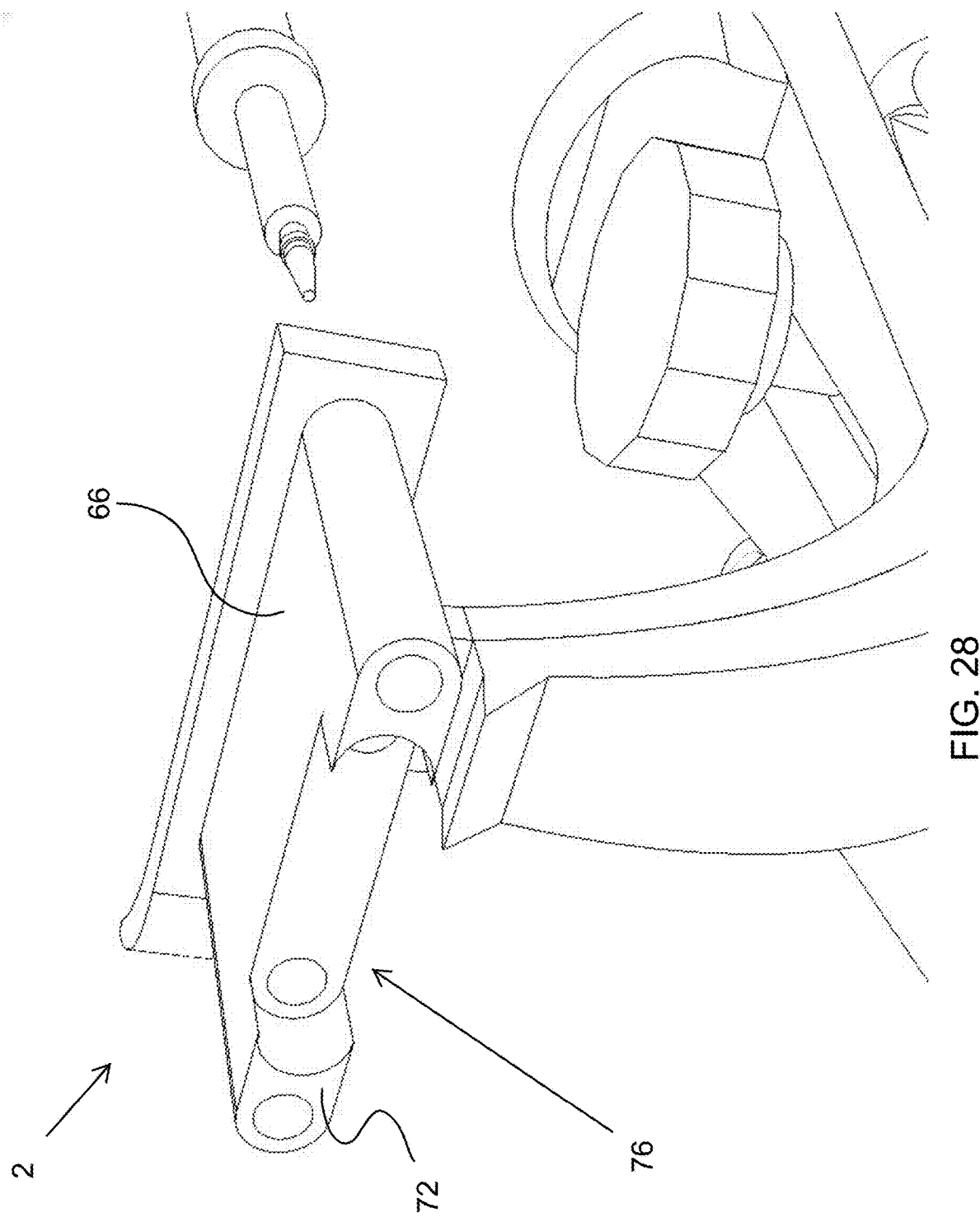
FIG. 28 is a partial isomeric view the bone surgery tool as presently disclosed, with a second embodiment of the cartridge for different shaped implants, and with the head, shoulder and jaw not shown for clarity in depicting the second cartridge embodiment.
Figure 29:
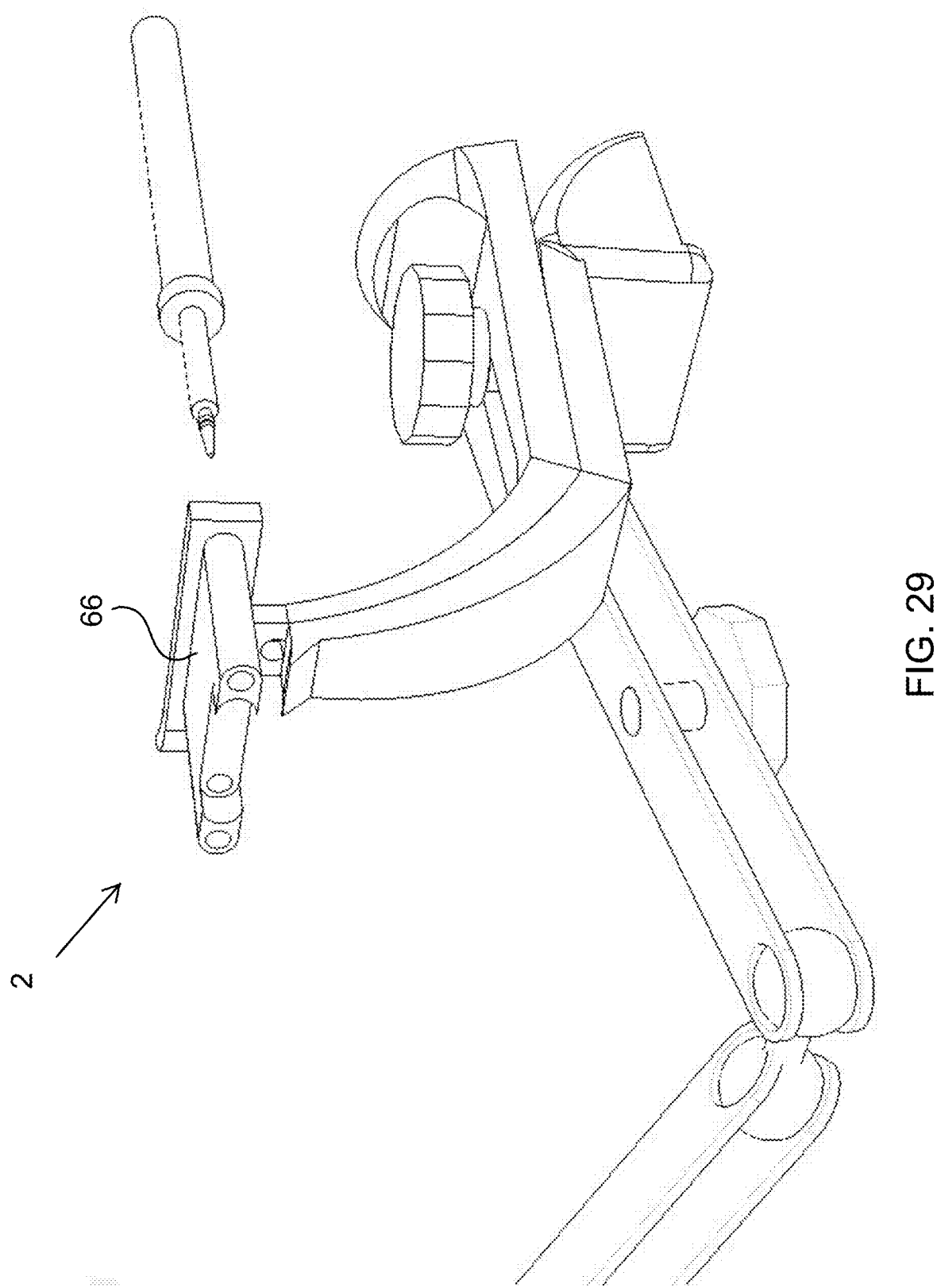
FIG. 29 is an isomeric view of the bone surgery tool in FIG. 28.

On each lateral side of the exterior of the head 14 is attached a buffer 96. A front facing portion of the buffer 96 is preferably shaped into two bumpers 98 each. The bumpers 98 can take a variety of shapes that achieve purpose of the invention. The bumpers 98 in the embodiment shown are semicircular, with the convex portion facing forward. This design urges the bone 28 into a vertically central location with respect to the slot 16. The bumpers 98 preferably have cut out portions 100 that better allow the bumpers 98 to elastically collapse and deform, cushioning the bone 28 while being captured and engaged by the bone surgery tool 2. Because bones can be fragile, the bumpers 98 help protect the bone 28 against the forces applied by the jaw 10 and head 14, including bending moments. As can be seen in FIG. 21, the bumpers 98 preferably extend further forward than any portion of the forward edge of the head 14. This causes the bone 28 to come into contact with the bumpers 98 first before hitting the firm material of the head 14. In the embodiment shown, the bumpers 98 are constructed of a synthetic rubber, providing both a low Young's modulus for elastic cushioning (preferably less than 2, and, more preferably less than 1, most preferably less than 0.1) and has high friction to better grip the bone 28.

To the rear and on the bottom surface of the head is an access 108 to the tunnel entrance defined in an abutment 110. The abutment abuts the top of the sliding neck portion of the sliding arm, the bottom of the head, and, when in the engaged position, the rear face of the shoulder The drill 86 that is used to drill the holes in the bone 28 for attaching the implant 64 has a drill body 102, a drill shield 104, and a drill bit 106. The drill shield 104 will preferably be arranged to allow a length of bit 106 to extend through the cartridge bore 78 and screw holes 68 along the drill passageway 84 and only partially into the bone 28 before the drill shield 104 contacts the rear face of the cartridge 66, preventing further insertion. In a preferred embodiment, the length of bit 106 extending past the drill shield 104 is adjustable for different depths of drill holes in the bone 28. The drill bit 106 is sized to fit in the length of the drill passageway. Similarly, a screwdriver that is used to screw in screws will preferably have a wider body, a neck that can fit in the length of the drill passageway, and a skirt that will prevent over insertion. In one embodiment, the screw is attached to the screw driver and is designed to shear off of the screw driver when fully set.

Procedure for using of the bone surgery tool 2 to affix an implant 64 to a bone 28. According to one embodiment, the bone surgery tool 2 is used to affix an implant 64 on an animal's bone 28 as follows. The order of each of the following steps is not necessarily required. Place the animal 26 on the surgical surface 24. Loosen the sliding arm lock 54, grasp the helve 57 and pull back on the ridge 59, pulling the sliding arm 12 back and thus pulling the head 14 back from the jaw 10 and providing space therebetween. Tighten the sliding arm lock 54. Grasp the handle 18 and loosen the clamps on the adjustable bracing, allowing the bone surgery tool to manipulated in 3 dimensions in space. Press the jaw 10 into the animal directly below the bone to be operated on, and then pull up and back, partially or fully seating the bone in the jaw 10. Tighten the clamps on the adjustable bracing 22. Press on the push surface 61, urging the head 14 forward towards the bone 28. When the bumpers 98 contact the bone 28, ease the head 14 forward a little further until the bumpers 98 are compressed into the cutout portions 100 and the bone 28 is securely seated between the jaw 10 and head 14. Tighten the sliding arm lock 54. Remove the handle 18.

If needed, loosen the cartridge lock 88. Insert an implant 64 into the slot 16 from the rear opening 60 until it contacts the snap retainers 74 adjacent to the front opening 62 of the slot 16. Insert a cartridge 66 into the slot 16 from the rear opening 60 until it contacts the implant 64, and the cartridge collar abuts the rear face of the head 14. Tighten the cartridge lock 88. The cartridge 66 and implant 64 may be loosely attached to one another and loaded together as a single unit, such that they break apart from one another when the cartridge 66 is secured to the bone 28 and the cartridge/bone 28, 64 is pulled from the bone surgery tool 2. The implant 64 and cartridge 66 may be loaded into the head at the beginning of the process or after the bone 28 is secured between the jaw 10 and the head 14, or any point in-between.

Insert a drill 86 with a bit 106 attached into one of the drill passageways 84 at a cartridge bore 78 from the rear side of the cartridge 66, through the cartridge 66, through a screw hole 68 in the implant 64 until the bit 106 comes into contact with the bone 28. Drill a first hole to a desired depth, with the drill shield 104 preferably positioned to stop the drill 86 automatically when the desired depth is reached. Remove the drill 86 from the first hole and repeat drilling additional holes in additional drill passageways 84 without needing to move anything with the bone surgery tool 2. Insert a screwdriver and mounted screw into one of the drill passageways 84 at a cartridge bore 78 from the rear side of the cartridge 66, through the cartridge 66, through a screw hole 68 in the implant 64 until the screw comes into contact with the hole drilled in the bone 28. Screw the screw into the bone 28, urging the implant 64 toward the bone 28 and attaching the implant 64 to the bone. Remove the screwdriver from the first hole and repeat with screwing in new screw in additional drilled holes in additional drill passageways 84 without needing to move anything with the bone surgery tool 2. The implant 64 may snap free from the snap retainers 74 as the implant is attached to the bone 28 during the screwing in step. Once all of the screws are screwed in, and the implant 64 is attached to the bone 28, re-attach the handle 18. Loosen the sliding arm lock 54, grasp the helve 57 and pull back on the ridge 59, pulling the sliding arm 12 back and thus pulling the head 14 back from the jaw 10 and providing space therebetween and releasing the hold the jaw 10 and head 14 together had on the bone 28. The implant 64 will remain with the bone 28 when the bone 28 is spaced from the head 14. Tighten the sliding arm lock 54. Grasp the handle 18 and loosen the clamps on the adjustable bracing 22, allowing the bone surgery tool to be manipulated in 3 dimensions in space. Press the jaw 10 into the animal, unseating the bone 28 from the jaw 10, then push down and pull the jaw 10 out of the animal 26. Tighten the clamps on the adjustable bracing 22.

Loosen the cartridge lock 88. Pull back on the hilt 82 and remove the cartridge 66 from the slot 16 from the rear opening 60.

Procedure to cut a bone 28 with a Gigli saw. Once the bone 28 is retained between the jaw 10 and head 14, insert a first end of the saw wire through the access 108 and into the tunnel entrance 42 of the tunnel groove 44. Continue to thread the wire into the tunnel entrance 42 until the first end of the wire emerges out of the groove exit 50. Attach saw handles onto the wire if desired. Then grasping each end of the wire, pull back while reciprocating the wire in one direction and then the other, cutting through the bone 28. Once the bone 28 is cut through, pull the wire out of either the tunnel entrance 42 or the groove exit 50.

Figure 30:
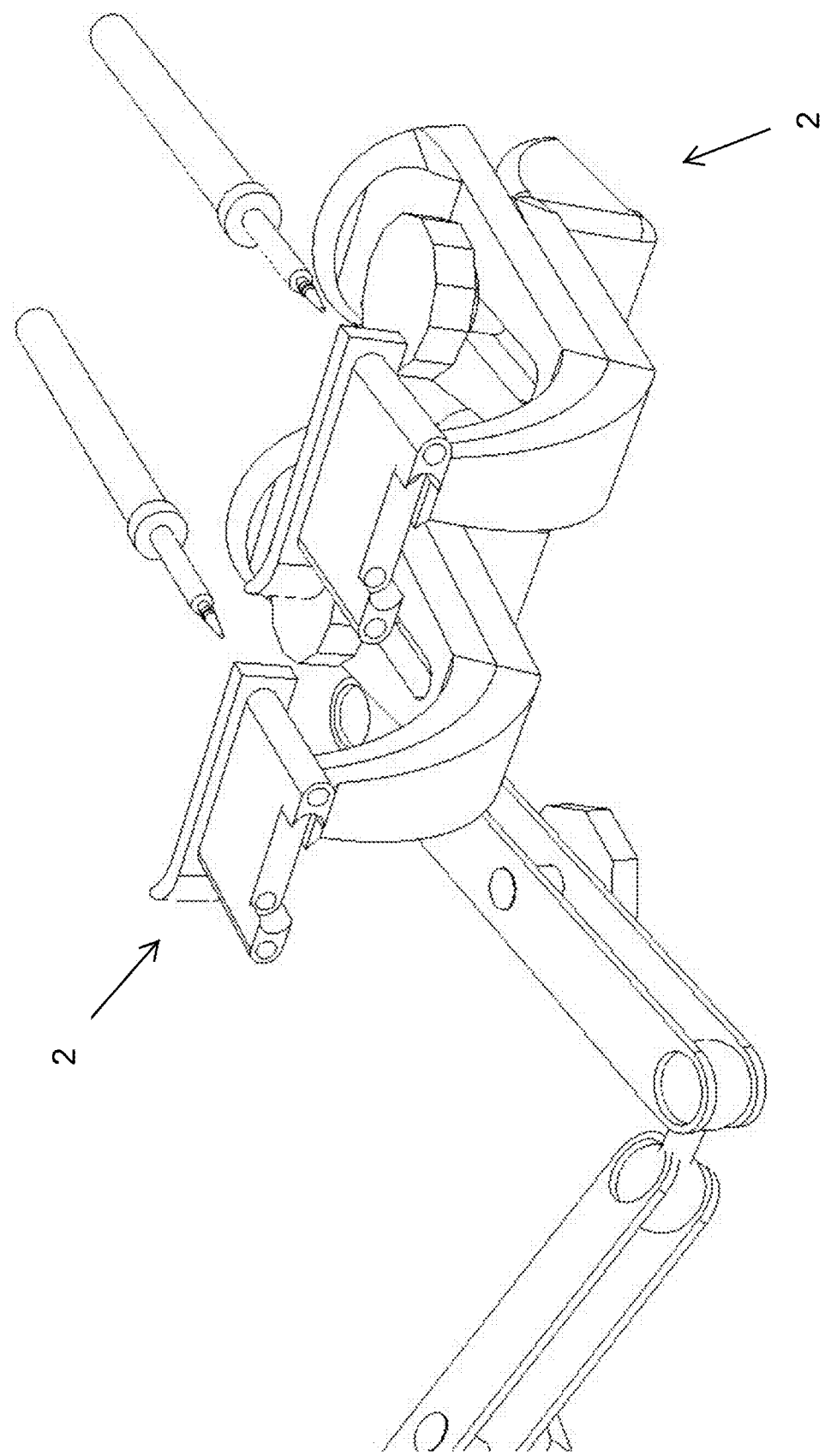
FIG. 30 is an isomeric view of a second embodiment of the bone surgery tool where two bone surgery tools are joined on a same adjustable bracing or a same surgical surface for operating on larger bones.

As shown in FIG. 30, according to a further embodiment, two bone surgery tools may be used together when operating on a larger animal, such as a cat or dog, or human for example. Each bone surgery tool could be separately attached to a surgical surface by separate adjustable bracings, or both could be connected to a single, preferably forked, adjustable bracing. Preferably a first bone surgery tool would engage a first portion of a fractured bone on a first side of the fracture, and the first bone surgery tool position would be locked. Then the second bone surgery tool would engage a second portion of the fractured bone on a second side of the fracture, and the second bone surgery tool position would be locked. Fine adjustments could then be made sequentially between the first and the second bone surgery tool.

In further embodiments, two jaws 10 could be provided on a single fixed arm 6 to provide four points of contact with a bone 28, and reduce the force delivered by using only one jaw 10 and three points of contact. The two jaws 10 would preferably be spaced from one another, more preferably aligned with or close to the bumpers 98.

In constructing the bone surgery tool 2, the base 4, fixed arm 6 and sliding arm 12 are preferably made of strong materials, such as a metal, like steel, stainless steel, aluminum, or titanium, or alloy, or a plastic such as Acetal Copolymer (POM-C), Acrylic (PMMA), Polycarbonate (PC), Polyether Ether Ketone (PEEK), Polypropylene (PP), Polyphenylsulfone (PPSU), Polyethylene (PE), Ultra High Molecular Weight PE (UHMW), Polytetrafluoroethylene (PTFE), Polysulfone (PSU), Polyphenylene Sulfide (PPS), Polyvinylidene Fluoride (PVDF), Polyetherimide (PEI), Polyphenylene Oxide (PPO), or combinations thereof, for example. The bumpers are preferably constructed of softer elastic elements or softer preparations of polymers than the head 14, such as rubber, Acrylonitrile Butadiene Styrene (ABS), PE, Low-density polyethylene (LDPE), and Polyamide (PA), or combinations thereof, for example. In one embodiment, the jaw 10 and shoulder 8 are semi-elastic allowing some bending about the shoulder when loading the bone 28, but still firm enough to securely hold the bone when the head 14 is engaged with the jaw 10 and bone 28.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Reference Numbers 2 bone surgery tool
4 base
6 fixed arm
8 shoulder
10 jaw
12 sliding arm
14 head
16 slot
18 handle
20 brace mount
22 adjustable bracing
24 surgical surface
26 animal
28 bone
29 pin
30 fixed neck
31 tail
32 top shoulder surface
34 bottom shoulder surface
36 track
38 channels
40 blocks
42 tunnel entrance
44 tunnel groove
46 tunnel groove path
48 radially inner surface of the jaw
20 groove exit
51 1st chamfered edge
52 sliding neck
53 2nd chamfered edge
54 sliding arm lock
55 3rd chamfered edge
56 slit path
57 helve
58 inner wall
59 ridge
60 rear opening
61 push surface
62 front opening
64 implant
66 cartridge
68 screw holes
70 cartridge insert
72 leading edge of cartridge insert
74 snap retainers
76 implant recess
78 cartridge bore
80 cartridge collar
82 hilt (of cartridge)
84 drill passageway
86 drill
88 cartridge lock
90 threaded shaft
92 threaded port
94 notch
96 buffer
98 bumper
100 cut out portions
102 drill body
104 drill shield
106 bit (drill)
108 access (to tunnel entrance)
110 abutment Wherefore, we claim:

1. A bone surgery tool comprising:
a base;
a fixed arm fixed to the base, the fixed arm comprising a shoulder and a jaw, wherein the shoulder comprises first and second tracks positioned on opposing sides of the shoulder;
a sliding arm releasably fixable to the base, the sliding arm comprises a head having a slot;
a cartridge releasably coupled to the slot, wherein the cartridge has one or more bore holes;
an implant, wherein the implant has one or more screw holes alignable with the one or more bore holes;
one or more snap retainers adjacent a front entrance of the slot for releasably coupling the implant to the head of the sliding arm; and
a first block and a second block each positioned on a bottom surface of the head, wherein the first block comprises a first channel and the second block comprises a second channel, and wherein the first and second tracks engage the first and second channels respectively when the sliding arm moves toward the fixed arm.

2. The bone surgery tool of claim 1, further comprising a cartridge lock that releasably holds the cartridge in a fixed position relative to the head.

3. The bone surgery tool of claim 1 further comprising a sliding arm lock that releasably holds the sliding arm in a fixed position relative to the fixed arm.

4. The bone surgery tool of claim 1 further comprising a first and a second buffer positioned on respective first and second lateral exterior surfaces of the head.

5. The bone surgery tool of claim 4, wherein the first and second buffers each comprise a bumper extending forward from the head toward the jaw.

6. The bone surgery tool of claim 5 wherein each bumper has a cutout portion.

7. The bone surgery tool of claim 6 wherein each bumper is shaped with two substantially semicircular cross sections, with a convex portion of each facing away from a rear opening of the slot.

8. The bone surgery tool of claim 4 further comprising a tunnel groove for sawing a bone, the tunnel groove running from a rear facing surface of the shoulder as a tunnel, and transitions to a groove on a radially inner facing surface of the jaw, and exits at a groove exit defined in the jaw.

9. The bone surgery tool of claim 4 wherein the shoulder has a substantially planar top surface that merges into the jaw.

10. The bone surgery tool of claim 9 wherein the jaw curves around in a substantially circular shape defining an arc of between one half and one sixth of a circumference of a circle.

11. The bone surgery tool of claim 10 further comprising a removable handle.

12. The bone surgery tool of claim 11 further comprising a helve adjacent a rear portion of the sliding arm.

13. The bone surgery tool of claim 12 wherein the helve includes a push surface facing substantially away from the head and a ridge.

14. A method for conducting bone surgery on an animal using the bone surgery tool of claim 1 comprising a base, a fixed arm fixed to the base, the fixed arm including a shoulder and a jaw, a sliding arm releasably fixable to the base, the sliding arm including a head that receives an implant and a cartridge in a slot, the method comprising:
    hooking the bone with the jaw;
    moving the head toward the jaw capturing the bone;
    accessing the bone with a drill through cartridge bores in the cartridge, and drilling holes;
    accessing the bone with a self-shearing screw attached to a screw driver through cartridge bores in the cartridge, and attaching the implant to the bone; and
    moving the head away from the jaw releasing the bone.

15. A bone surgery tool comprising:
    a base;
    a fixed arm fixed to the base, the fixed arm comprising a shoulder and a jaw, wherein the shoulder comprises first and second tracks positioned on opposing sides of the shoulder;
    a sliding arm releasably fixable to the base, the sliding arm comprising a head;
    a cartridge sized to be received by a slot defined by an inner wall of the head;
    one or more snap retainers adjacent a front entrance of the slot sized to releasably retain an implant;
    wherein the cartridge has a plurality of bore holes defined within that align to a respective plurality of screw holes in an implant when the implant and cartridge and implant are both loaded into the slot;
    a cartridge lock that releasably holds the cartridge in a fixed position relative to the head;
    a sliding arm lock that releasably holds the sliding arm in a fixed position relative to the fixed arm;
    a first block and a second block each positioned on a bottom surface of the head, wherein the first block comprises a first channel and the second block comprises a second channel, and wherein the first and second tracks engage the first and second channels respectively when the sliding arm moves toward the fixed arm;
    a first and a second buffer positioned on respective first and second lateral exterior surfaces of the head, wherein the first and second buffer each comprise a bumper
    extending forward from the head toward the jaw, wherein each bumper has a cutout portion, and each bumper is shaped with two substantially semicircular cross sections, with a convex portion of each facing away from a rear opening of the slot;
    a tunnel groove for sawing a bone, the tunnel groove running from a rear facing surface of the shoulder as a tunnel, and transitions to a groove on a radially inner facing surface of the jaw, and exits at a groove exit defined in the jaw;
    a handle removable from the base;
    a helve adjacent a rear portion of the sliding arm, the helve including a push surface facing substantially away from the head and a ridge;
    the cartridge has a cartridge insert that is sized to fit into the slot, a cartridge collar at a rear portion of the cartridge that flares outward substantially orthogonally from the cartridge insert, wider than the slot, and a hilt that extends off on one side of the cartridge;
    a brace mount connected to the base; and
    an adjustable bracing that connects the brace mount to a surgical surface.

16. A bone surgery tool comprising:
    a base;
    a fixed arm connected to the base, the fixed arm comprising a shoulder portion and a jaw portion, wherein the shoulder comprises first and second tracks positioned on opposing sides of the shoulder;
    a sliding arm releasably fixable to the base, the sliding arm comprises a head having a slot;
    a cartridge releasably coupled to the slot, wherein the cartridge has one or more bore holes;
    an implant having one or more screw holes alignable with the one or more bore holes of the cartridge; and
    a first block and a second block each positioned on a bottom surface of the head, wherein the first block comprises a first channel and the second block comprises a second channel, and wherein the first and second tracks engage the first and second channels respectively when the sliding arm moves toward the fixed arm.

* * * * *